(12) United States Patent
Kassab et al.

(10) Patent No.: US 9,566,073 B2
(45) Date of Patent: Feb. 14, 2017

(54) DEVICES, SYSTEMS, AND METHODS FOR ATRIAL APPENDAGE OCCLUSION

(71) Applicant: CVDevices, LLC, Zionsville, IN (US)

(72) Inventors: Ghassan S. Kassab, Zionsville, IN (US); Jose A. Navia, Sr., Buenos Aires (AR)

(73) Assignee: CVDevices, LLC, San Diego, CA (US)

( * ) Notice: Subject to any disclaimer, the term of this patent is extended or adjusted under 35 U.S.C. 154(b) by 269 days.

(21) Appl. No.: 14/177,803

(22) Filed: Feb. 11, 2014

(65) Prior Publication Data

US 2014/0228877 A1    Aug. 14, 2014
US 2016/0287850 A9    Oct. 6, 2016

Related U.S. Application Data

(63) Continuation of application No. 12/522,674, filed as application No. PCT/US2008/000838 on Jan. 23, 2008, now Pat. No. 8,647,367.

(Continued)

(51) Int. Cl.
*A61B 17/08* (2006.01)
*A61B 17/12* (2006.01)
(Continued)

(52) U.S. Cl.
CPC ... *A61B 17/12122* (2013.01); *A61B 17/00491* (2013.01); *A61B 17/122* (2013.01); *A61B 17/1204* (2013.01); *A61B 17/12031* (2013.01); *A61B 17/0057* (2013.01); *A61B 17/12136* (2013.01); *A61B 2017/0065* (2013.01); *A61B 2017/00292* (2013.01); *A61B 2017/00349* (2013.01); *A61B 2017/00867* (2013.01); *A61B 2017/00876* (2013.01); *A61B 2017/1205* (2013.01); *A61B 2017/306* (2013.01); *A61M 25/007* (2013.01)

(58) Field of Classification Search
CPC .......... A61B 17/12122; A61B 17/12031; A61B 17/12136; A61B 17/12186; A61B 17/12195; A61B 17/0057; A61B 17/00491; A61B 2017/00243; A61B 2017/0065; A61B 2017/00623; A61B 2017/00575; A61B 2017/1205; A61B 2017/00876; A61M 25/007; A61M 29/02
See application file for complete search history.

(56) References Cited

U.S. PATENT DOCUMENTS 6,152,144 A * 11/2000 Lesh ................. A61B 17/0057
                                              128/898
6,315,709 B1  11/2001 Garibaldi et al.
(Continued)

OTHER PUBLICATIONS

International Searching Authority, International Search Report, PCT/US2009/030222, dated Feb. 24, 2009.
(Continued)

*Primary Examiner* — Robert Lynch
(74) *Attorney, Agent, or Firm* — Reichel Stohry LLP; Mark C. Reichel; Natalie J. Dean

(57) ABSTRACT

Devices, systems and methods for atrial appendage occlusion. A device is described with respect to non-surgically occluding the left atrial appendage with minimal invasiveness. Additionally, a system and method are described for using the device to perform the left atrial appendage occlusion procedure.

14 Claims, 25 Drawing Sheets

Related U.S. Application Data

(60) Provisional application No. 60/881,831, filed on Jan. 23, 2007.

(51) Int. Cl.
*A61B 17/122* (2006.01)
*A61M 25/00* (2006.01)
*A61B 17/00* (2006.01)
*A61B 17/30* (2006.01)

(56) References Cited

U.S. PATENT DOCUMENTS

| | | |
|---|---|---|
| 6,919,067 B2 | 7/2005 | Filler et al. |
| 7,918,865 B2 | 4/2011 | Liddicoat et al. |
| 2003/0060756 A1* | 3/2003 | Hayman .......... A61B 17/00491 604/103.05 |
| 2003/0120337 A1 | 6/2003 | Van Tassel et al. |
| 2003/0208232 A1 | 11/2003 | Blaeser et al. |
| 2005/0090861 A1 | 4/2005 | Porter |
| 2005/0096501 A1 | 5/2005 | Stelzer et al. |
| 2006/0009801 A1 | 1/2006 | McGurk et al. |
| 2006/0020271 A1 | 1/2006 | Stewart et al. |
| 2006/0036284 A1 | 2/2006 | Bleaser et al. |
| 2006/0253129 A1 | 11/2006 | Liddicoat et al. |
| 2007/0149995 A1 | 6/2007 | Quinn et al. |
| 2007/0233239 A1 | 10/2007 | Navia et al. |
| 2008/0033241 A1* | 2/2008 | Peh .................... A61B 1/0008 600/109 |

OTHER PUBLICATIONS

International Searching Authority (ISA), Written Opinion of the ISA, PCT/US2009/030222, dated Feb. 24, 2009.

International Searching Authority, International Search Report, PCT/US2008/000838, dated Jul. 8, 2008.

International Searching Authority (ISA), Written Opinion of the ISA, PCT/US2008/000838, dated Jul. 8, 2008.

* cited by examiner

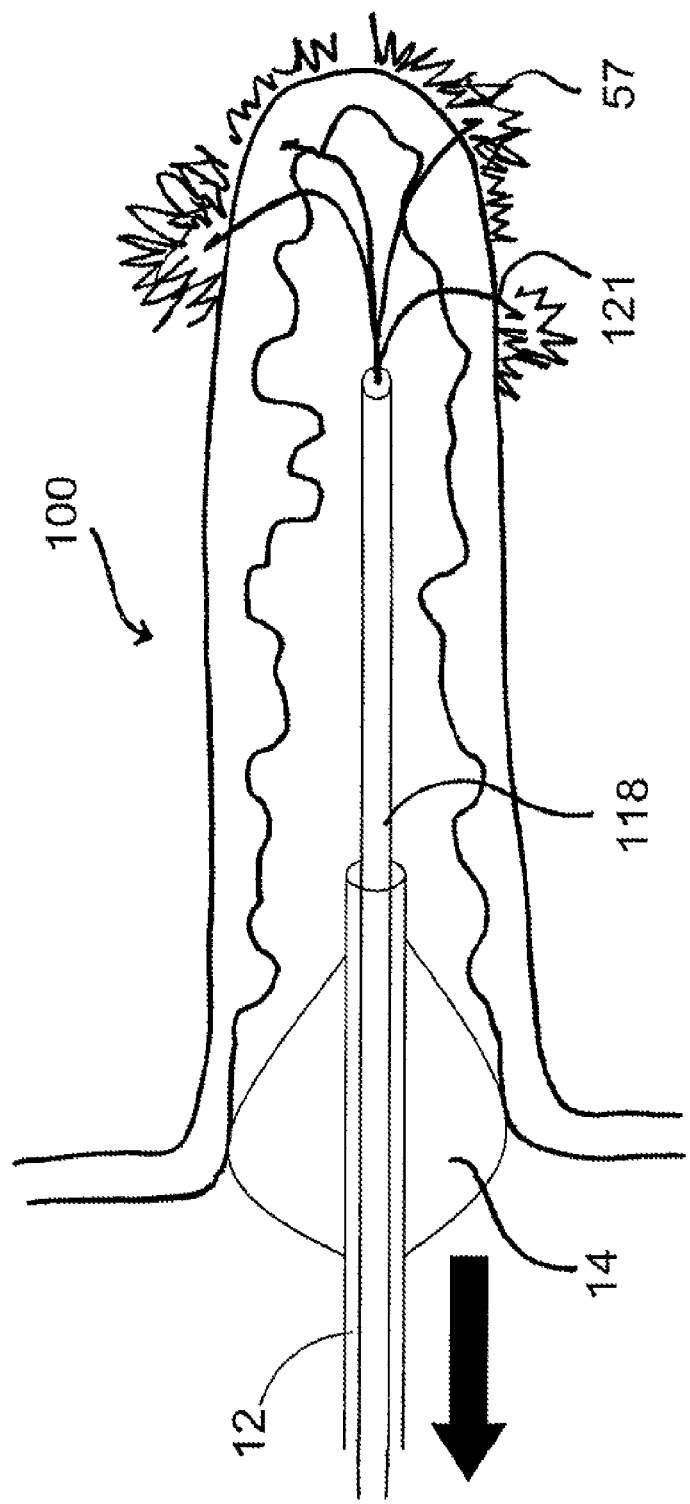

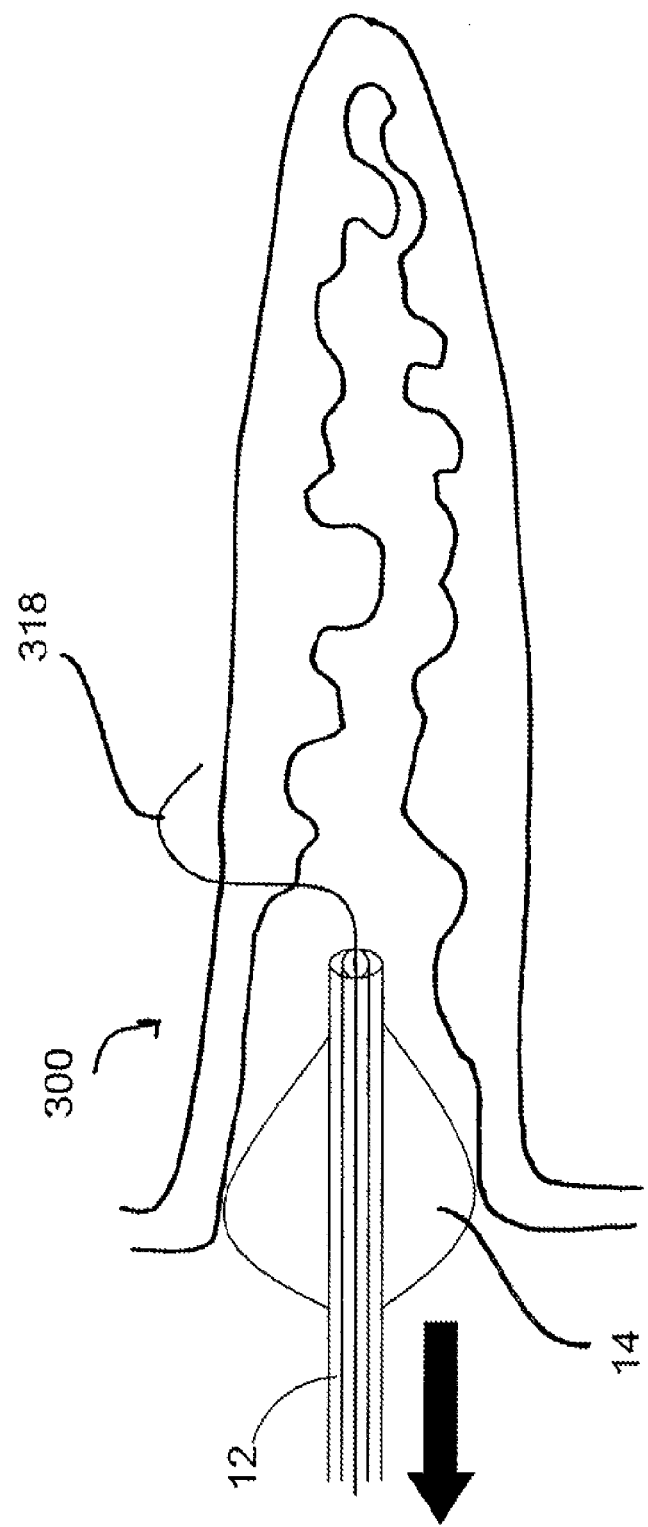

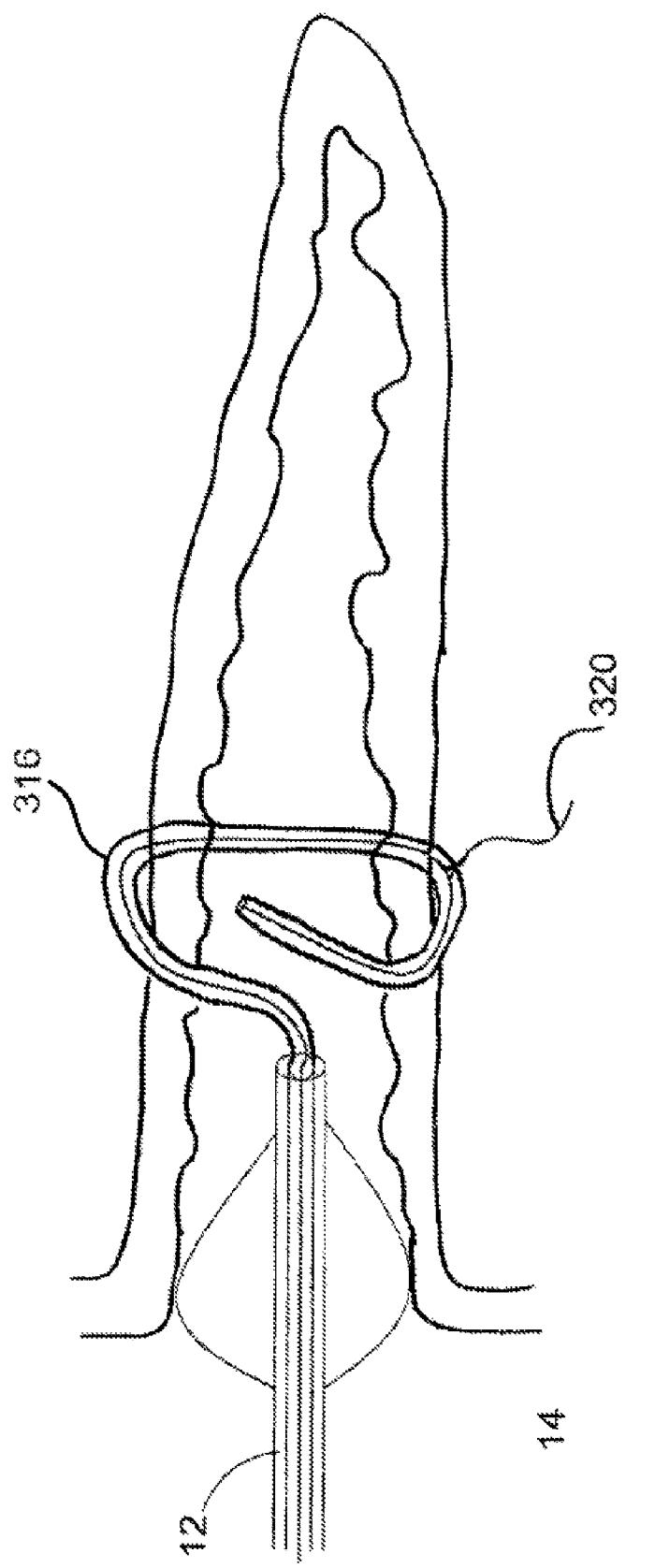

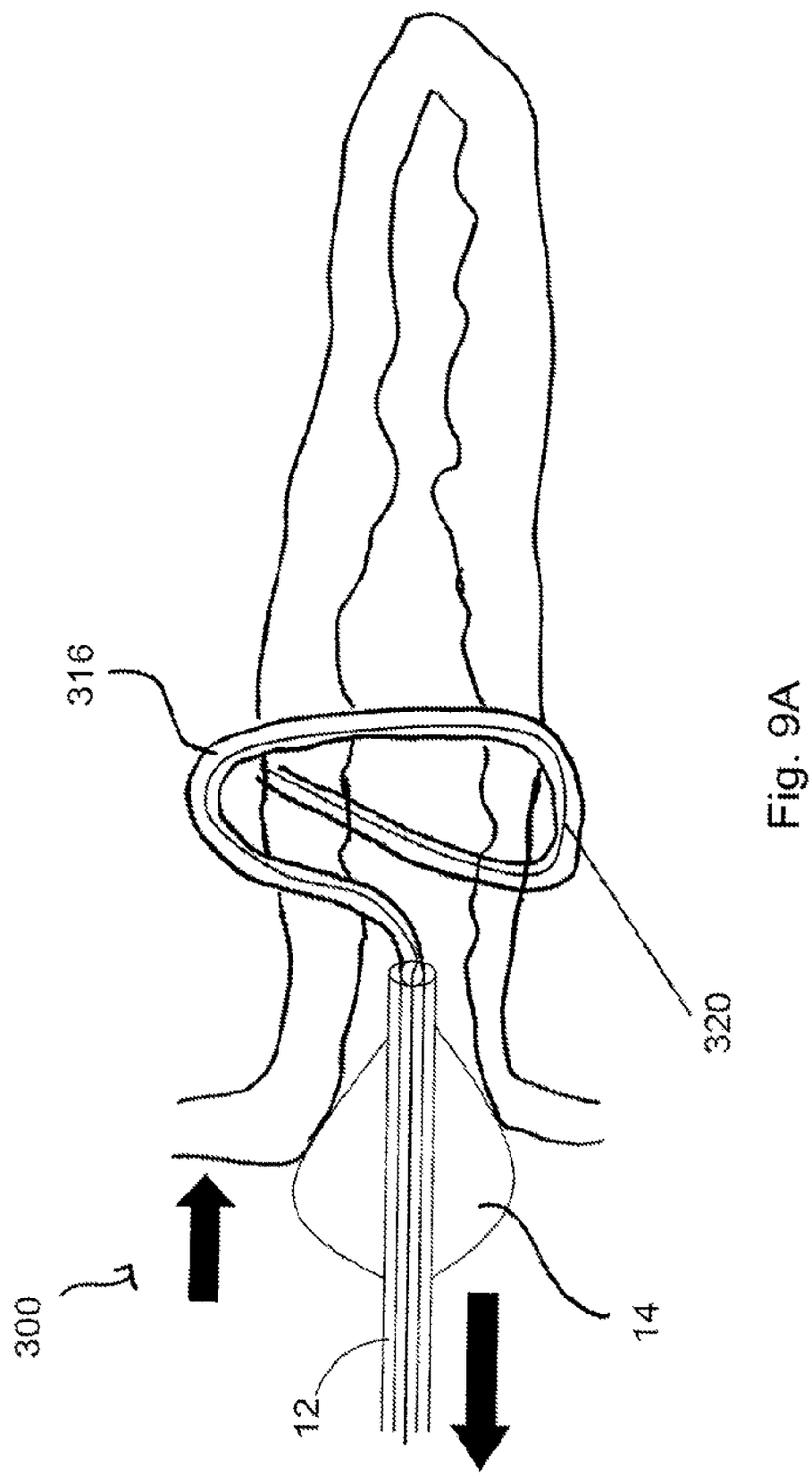

# DEVICES, SYSTEMS, AND METHODS FOR ATRIAL APPENDAGE OCCLUSION

PRIORITY

The present application is related to, claims the priority benefit of, and is a U.S. continuation application of, U.S. patent application Ser. No. 12/522,674, filed on Jul. 9, 2009 and issued as U.S. Pat. No. 8,647,367 on Feb. 11, 2014, which is related to, and claims the priority benefit of, International Patent Application Serial No. PCT/US2008/000838, filed on Jan. 23, 2008, which is related to, and claims the priority benefit of, U.S. Provisional Patent Application Ser. No. 60/881,831, filed on Jan. 23, 2007. The contents of each of these applications and issued patent are hereby incorporated by reference in their entirety into this disclosure.

BACKGROUND

Currently, 2.2 million patients in the United States suffer atrial fibrillation ("AF"). About half of these patients are considered to be at a high risk for stroke. The Stroke Prevention in Atrial Fibrillation trials (SPAF, SPAF II, SPAF III) have shown that chronic warfarin therapy reduces the risk of stroke by about 70%. Nevertheless, problems related with the long term use of anti-coagulation treatments are well known. It has been shown that up to two-thirds of eligible AF patients do not receive warfarin treatment. This can be at least partly attributed to the fact that warfarin is difficult to dose as it is known to interact with many commonly-used medications and other chemicals that may be present in appreciable quantities in food. Accordingly, safer options are desirable.

AF is frequently diagnosed in elderly patients and is responsible for more than 15% of all strokes. This percentage grows to almost 25% in women and men older than 80 years of age. Dilation of the left atrium and a reduction of blood flow velocity, especially in the left atrial appendage, is commonly seen with AF. Atrial contraction is responsible for blood ejection out of the left atrium and appendage. The dysfunction of the left atrial contraction is followed by blood stagnation, especially at the level of the atrial appendage. It has been demonstrated by means of echocardiography and autopsy studies that more than 90% of all thrombi in patients with non-rheumatic AF beginning in the left atrium, appear in the left atrial appendage. Thrombus formation elevates the threat of stroke by three-fold.

The left atrial appendage ("LAA") is an embryonic remnant of the left atrium that grows during the third week of pregnancy. The left atrial cavity develops soon after and is produced from an outgrowth of the pulmonary veins. The diameter of the LAA ostium into the left atrial cavity is about 1 to 4 cm and is positioned between the left upper pulmonary vein and the left ventricle. The left axis deviation orifice, width, and length are typically about 0.7 to 2 cm, 0.9 to 3.4 cm, and 1.3 to 4 cm, respectively. The circumflex branch and the left coronary artery runs close to the base of the LAA ostium.

The LAA is a long structure with tubular or hooked shape of variable morphology and size. The LAA wall is trabeculated including muscle bars, known as pectinate muscles. The cavities between the pectinate muscles emerge as "branches" (lobes), "twigs", or "fine structures." LAA closure may be an option in patients who cannot receive anticoagulation treatment as a result of contraindications or conditions in which the hemorrhage risk is greater than the potential medical benefit.

One of the convention options of treating LAA closure is surgery. However, it is unsuitable for the same high-risk patients who are poor candidates for warfarin therapy. Accordingly, a safe, accurate and minimally invasive procedure is needed to occlude the LAA.

BRIEF SUMMARY

Embodiments disclosed herein comprise devices and methods of LAA occlusion that do not require surgery and avoid many of the risks associated with current methods of LAA occlusion. In one embodiment, a standard trans-septal sheath kit is utilized for percutaneous transluminal access. A balloon catheter at the tip of the shaft is inflated for occlusion of the LAA orifice or ostium. Thereafter, a three-lumen catheter with a pigtail tip designed for dual functionality is utilized for suction first, which collapses the LAA, then injection of magnetic glue to seal the collapsed LAA.

In another exemplary embodiment of the present invention, a plurality of wire needles are employed to puncture the LAA, and thereafter apply magnetic beads thereon. In one embodiment, biologic glue may also be employed to seal the LAA. In yet another embodiment, an umbrella-like clip assembly composed of magnetic rods is introduced through a catheter to the outside of the LAA. The configuration of the magnetic rods may be opened to receive the exterior portion of the LAA, and thereafter closed around the LAA and secured to a magnetic substance inside the LAA. In one embodiment, the magnetic rods employ magnetic forces to attract and secure proper placement of the device In still another exemplary embodiment, a pigtail catheter is used to introduce a wire comprised of a shape memory alloy around the base of the LAA. In one embodiment, a nitinol wire is used. In application, the wire may be tied around the outside of the base of the LAA, thereby maintaining the seal.

BRIEF DESCRIPTION OF THE DRAWINGS

FIGS. 3B-D shows side views of the needle wires of the occlusion assembly of FIG. 3A applied to treat a left atrial appendage;

FIGS. 7-9B shows a side view of the pigtail catheter of FIGS. 6A-6C as applied to treat a left atrial appendage.

DETAILED DESCRIPTION

Figure 1A:
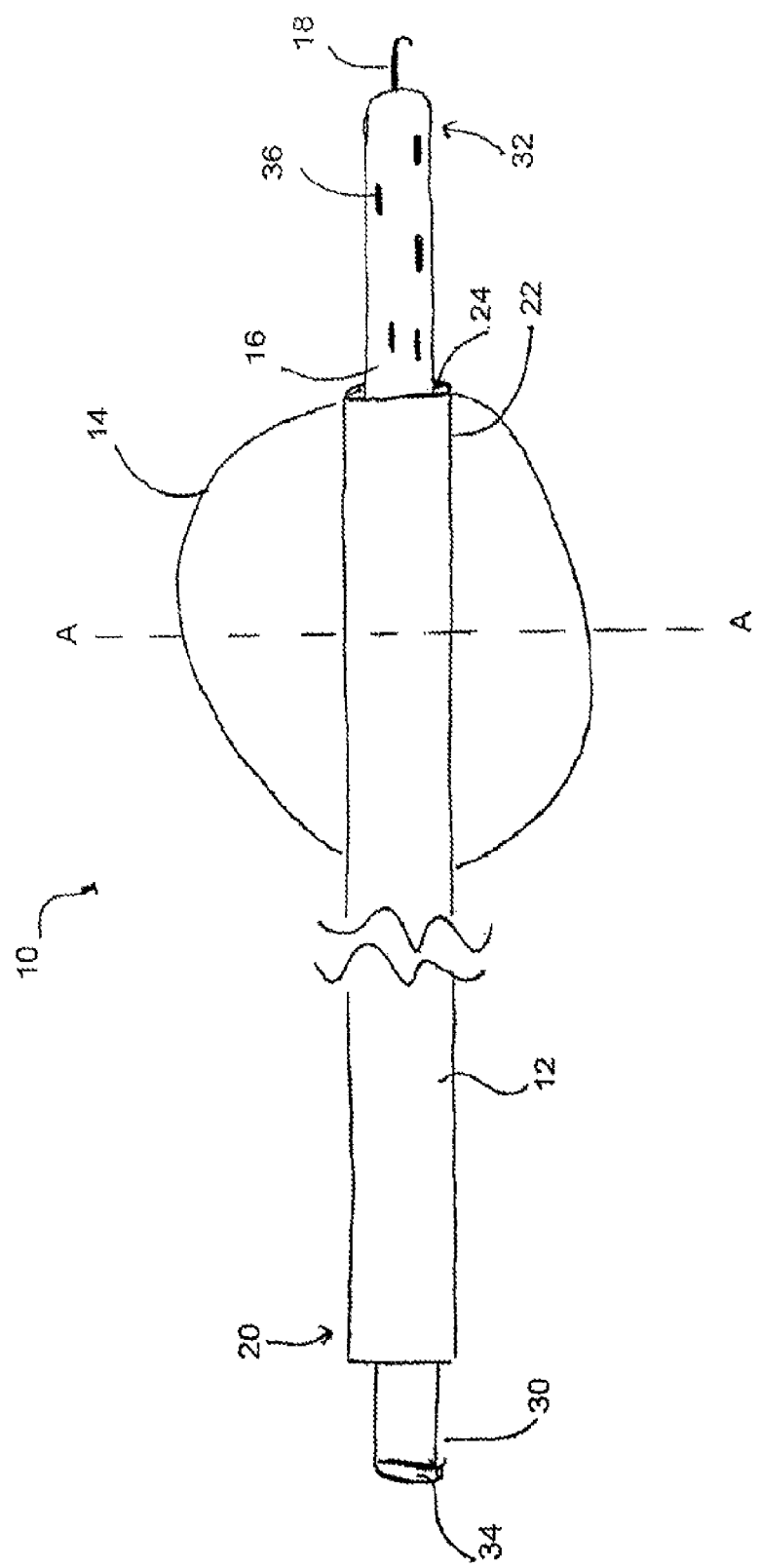
FIG. 1A shows a side view of at least one embodiment of an occlusion assembly.

Reference will now be made to the embodiments illustrated in the drawings and specific language will be used to describe the same. It will nevertheless be understood that no limitation of scope is intended by the description of these embodiments.

FIG. 1 shows a side view of one embodiment of an occlusion assembly 10 for closing a left atrial appendage. Specifically, the assembly 10 is configured for placement within the left atrial appendage ("LAA") and is delivered non-surgically through the use of catheterization and percutaneous transluminal access.

The occlusion assembly 10 comprises a shaft 12, a balloon 14, a catheter 16, and a guidewire 18. The shaft 12 comprises an elongated catheter shaft having a proximal end 20, a distal end 22, and an interior 24. Both the proximal end 20 and the distal end 22 of the shaft 12 are open and in communication with the interior 24. The interior 24 of the shaft 12 extends throughout the length of the shaft 12 and provides a channel through which the distal end 22 of the shaft 12 may be accessed when positioned within a body.

The balloon 14 is coupled with the distal end 22 of the shaft 12 and can comprise any balloon catheter tip known in the art. The balloon 14 may comprise a tube or other inflation means (not shown) coupled therewith to facilitate the inflation and deflation of the balloon 14 when positioned within the body. The balloon 14 can be configured in a range of sizes to accommodate the anatomy of the left atrial appendage. In one embodiment, the balloon 14 comprises a flattened-disk configuration, however it will be understood that the balloon 14 can comprise various shapes and forms that will assist in the temporary closing and sealing of the LAA cavity, including, without limitation, a hemisphere shape and a wine-bottle cork shape.

The occlusion assembly 10 further comprises a guidewire 18. The guidewire 18 is configured to be inserted through the interior 24 of the shaft 12 and may be any standard guidewire known in the art. In one embodiment, the guidewire 18 functions to facilitate navigation of the shaft 12 and catheter 16 into the LAA. Use of the guidewire 18 enables more effective navigation of the occlusion assembly 10 and prevents damage to the atrial or appendage walls.

In one approach, the procedure can be performed under local anesthesia and conscious sedation. The shaft 12 and the balloon 14 coupled therewith are inserted through the femoral vein and advanced to the right atrium of the heart. Thereafter, a trans-septal puncture is made at the level of the fossa ovalis area to access the left atrium. After the shaft 12 and the balloon 14 are positioned within the left atrium, the guidewire 18 is inserted into the LAA, visualized by fluoroscopy or transesophageal echocardiography, and the shaft 12 is threaded over the guidewire 18 such that the balloon 14 is positioned adjacent to the ostium of the LAA. When the balloon 14 is properly positioned, as shown in FIG. 1A, the balloon 14 is inflated to occlude the LAA orifice.

After the shaft 12 and the balloon 14 are properly positioned with respect to the LAA, the catheter 16 may be introduced. The catheter 16 of the occlusion assembly 10 comprises an elongated, flexible tube having an exterior wall, a proximal end 30, a distal end 32, a hollow interior 34, and at least one opening 36 disposed through the exterior wall. The proximal end 30 of the catheter 16 is in communication with the interior 34, and the interior 34 extends throughout the length of the catheter 16. Accordingly, the interior 34 of the catheter 16 provides a channel through which the distal end 32 may be accessed.

The catheter 16 is configured to be slidably positioned within the interior 24 of the shaft 12. For example, the distal end 32 of the catheter 16 can be inserted into the proximal end 20 of the shaft 12, advanced through the interior 24 of the shaft 12, and extended into the LAA cavity. In one embodiment, the catheter 16 comprises a length that is greater than the length of the shaft 12 such that the distal end 32 of the catheter 16 can conveniently be extended through the distal end 22 of the shaft and into the LAA cavity. Further, in at least one embodiment, the catheter 16 comprises a three-lumen pigtail catheter, such that the distal end 32 is tightly curled. This tightly curled configuration functions to prevent trauma in the event the proximal end 32 comes into contact with a vessel or organ wall as the catheter 16 is advanced through the body of a patient.

The distal end 32 of the catheter 16 comprises at least one opening 36 disposed therein. Each of openings 36 located on the distal end 32 is in communication with the interior 34 of the catheter 16 and comprises a configuration such that a force or substance can be transmitted therethrough. For example, in one embodiment, the at least one opening 36 comprises a suction port configured to aspirate an area adjacent to the catheter 16 when the at least one opening 36 is coupled with a vacuum source. In an alternative embodiment, the at least one opening 36 comprises a single opening at the distal end 32 of the catheter 16, configured such that the guidewire 18 or other device can be positioned therethrough. In yet another embodiment, the at least one opening 36 is configured to deliver a substance to the surrounding tissue, such as an adhesive or medicament. The number of openings 36 located on the distal end 32 of the catheter 16 may depend on the desired functionality of the occlusion assembly 10, and it will be understood that any number of openings 36 may be employed.

As previously described, the interior 34 of the catheter 16 extends from the proximal end 30 of the catheter 16 to the distal end 32 of the catheter 16. Further, the interior 34 is in communication with the at least one opening 36. Accordingly, the interior 34 of the catheter 16 can function as a conduit through which a force, device, and/or substance may be delivered to the at least one opening 36. For example, when a vacuum source, such as a syringe or other vacuum source, is coupled with the proximal end 30 of the catheter 16, the suctional force produced thereby can be communicated throughout the interior 34 of the catheter 16 and through the at least one opening 36 in communication therewith. In one embodiment, a syringe or other vacuum source (not shown) may be coupled with the proximal end 30 of the catheter 16 in order to provide appropriate suction throughout the interior 34 of the catheter 16. It will be understood that any type of vacuum source may be used to supply suction throughout the interior 34, such as a controlled vacuum system providing specific suction pressures. In another embodiment, an adhesive delivery device (not shown) is coupled with the proximal end 30 of the catheter 16. The adhesive delivery device may comprise any means for advancing an adhesive through the interior 34 of the catheter and through the at least one opening 36. For example, in one embodiment, the adhesive delivery device may be a clinician's hand when he or she applies force to a container of adhesive such that the adhesive is advanced through the interior 34 of the catheter 16. In an alternative embodiment, the adhesive delivery device may comprise a specifically designed mechanism for advancing the adhesive.

Figure 1B:
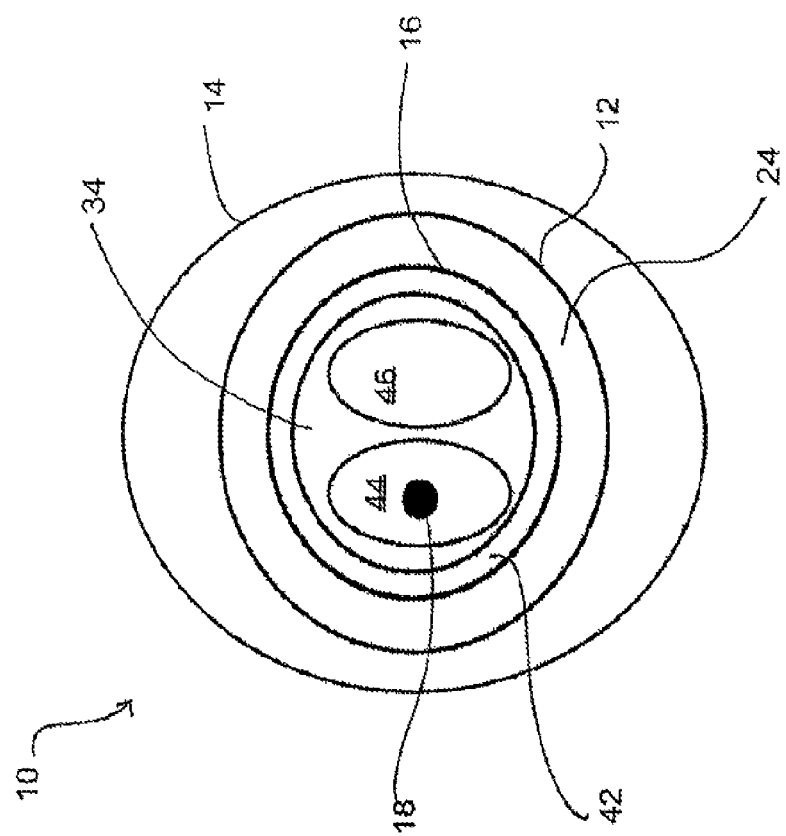
FIG. 1B shows a cross-sectional view of at least one embodiment of an occlusion assembly taken along line A-A of FIG. 1A.

Referring now to FIG. 1B, in one embodiment, the interior 34 of the catheter 16 comprises multiple lumens. In the embodiment shown in FIG. 1B, the occlusion assembly 10 comprises a triple-lumen pigtail catheter, wherein the interior 34 comprises a first lumen 42, a second lumen 44, and a third lumen 46. In this embodiment, the first lumen 42 is disposed around the circumference of the catheter 16 and the second and third lumens 44, 46 are disposed centrally within the interior 34. The second and third lumens 44, 46 are wholly surrounded by the first lumen 42. While this specific configuration is shown with respect to FIG. 1B, it will be appreciated that the interior 34 may comprise any number of lumens and the lumens can be arranged in any configuration.

The multiple lumens enable the catheter 16 to perform multiple functions without withdrawing the catheter 16 from the body or employing more than one device. For example, a plurality of openings 36 configured to aspirate a tissue may be in communication with the first lumen 42, a single opening 36 configured to receive the guidewire 18 therethrough may be in communication with the second lumen 44, and a plurality of openings 36 configured to deliver a substance to a tissue may be in communication with the third lumen 46. In this manner, the catheter 16 is capable of various functionalities including, without limitation, delivering suction to the cavity of the LAA, advancing the guidewire 18 to ensure accurate navigation throughout the body, and applying an adhesive to the LAA. It will be recognized that the catheter 16 may further comprise any combination of the aforementioned embodiments on a single device. In addition, the number of openings 36 located on the distal end 32 of the catheter 16 depend on the desired functionality of the occlusion assembly 10, and it will be understood that any number of openings 36 may be employed.

Figure 2A:
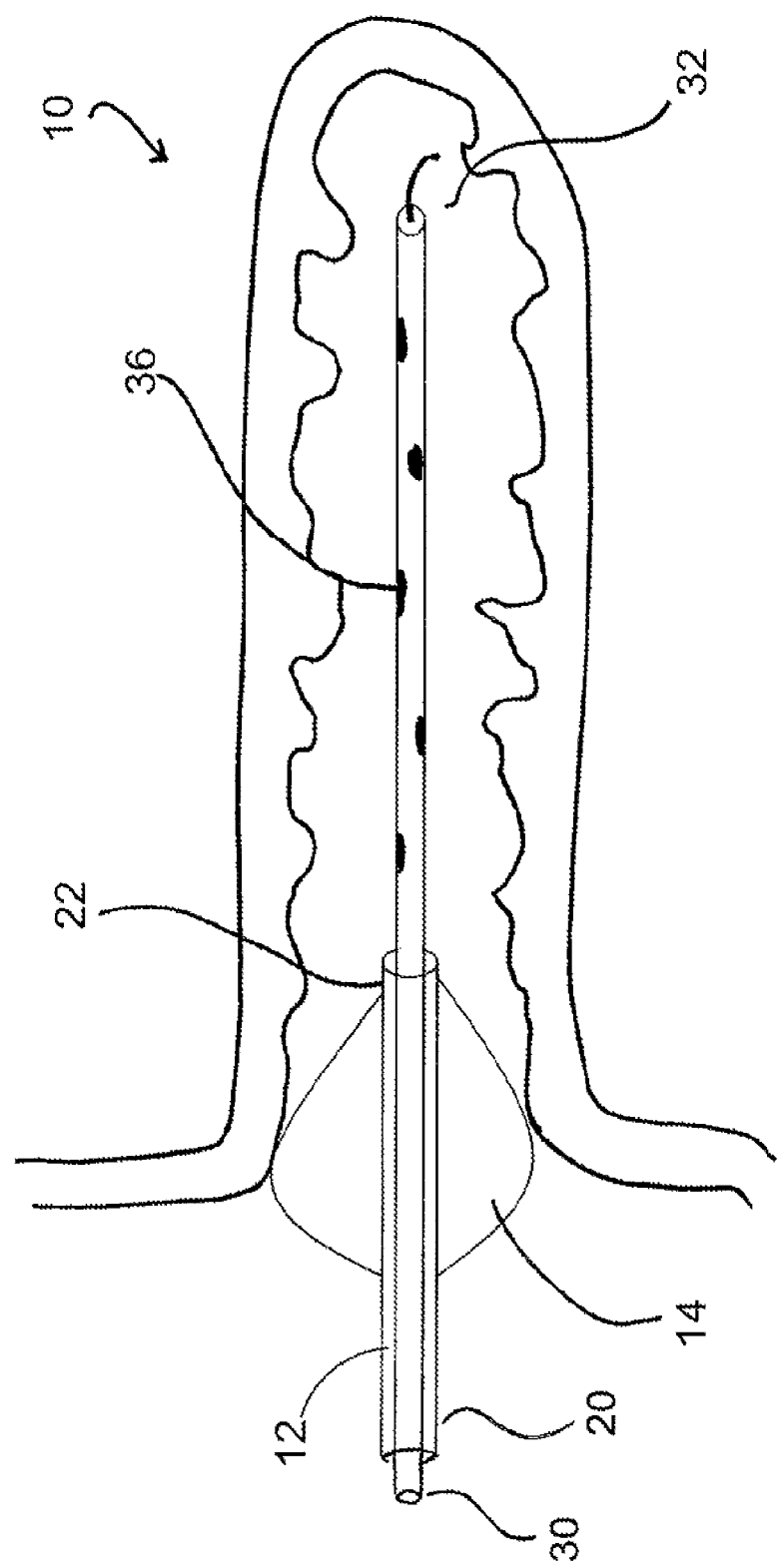
FIGS. 2A-2E shows a side view of the occlusion assembly of FIGS. 1A and 1B as applied to treat a left atrial appendage.

The operation of the occlusion assembly 10 will now be described with respect to the at least one embodiment of the catheter 16 shown in FIG. 2A. While this embodiment is described herein, it is understood that any of the embodiments of the catheters 16 described herein may be used to occlude a LAA.

Figure 2B:
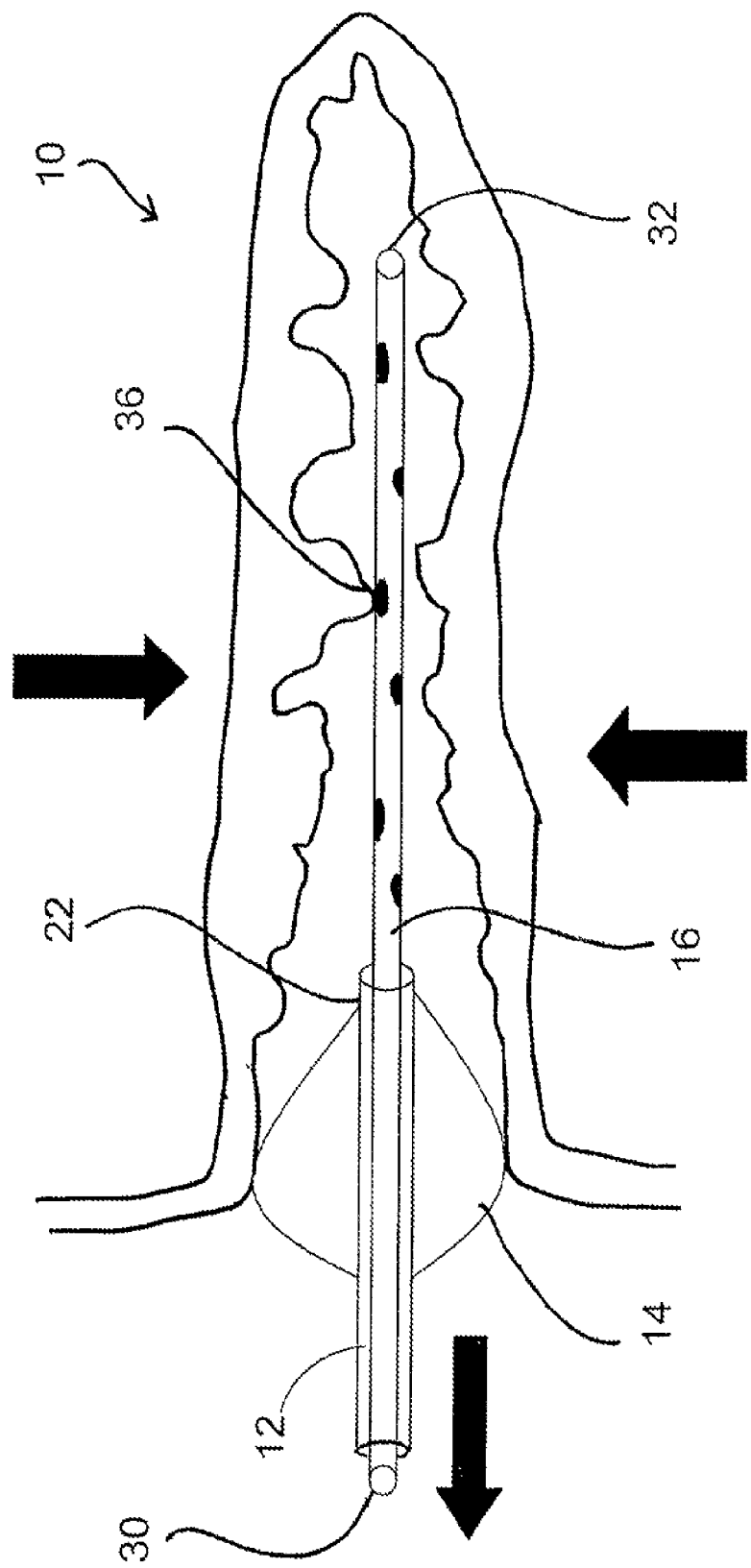

In operation, the guidewire 18 is threaded through the previously deployed shaft 12 and inserted into the cavity of the LAA, visualized by fluoroscopy or transesophageal echocardiography. After the guidewire 18 has accessed the cavity of the LAA, the distal end 32 of the catheter 16 is advanced through the distal end 22 of the shaft 12 and into the cavity of the LAA as shown in FIG. 2A. While maintaining the inflation of the balloon 14 occluding the LAA ostium, suction is initiated through the catheter 16. Specifically, a vacuum source is coupled with the first lumen 41 such that a vacuum is created therein. In this manner, the plurality of openings 36 function to aspirate the cavity of the LAA. This suctional force is maintained until a small amount of blood is removed from the LAA cavity and the LAA wall collapses as shown in FIG. 2B. After the LAA wall is completely collapsed, the suction is ceased. As the balloon 14 is occluding the LAA ostium and the LAA cavity is sealed, the collapse is maintained even in the absence of aspiration.

At this point, the catheter 16 is used to inject an adhesive 47 into the collapsed LAA cavity. In one embodiment the adhesive 47 comprises a biologic glue, however, the adhesive 47 can comprise any adhesive known in the medical arts. Accordingly, the occlusion assembly 10 may further comprise a delivery apparatus (not shown) for providing the adhesive 47 to the catheter 16. In one embodiment, the delivery apparatus is coupled with the third lumen 46 such that the adhesive 47 is advanced therethrough and applied to the cavity of the LAA through the at least one of opening 36 in communication therewith.

Figure 2C:
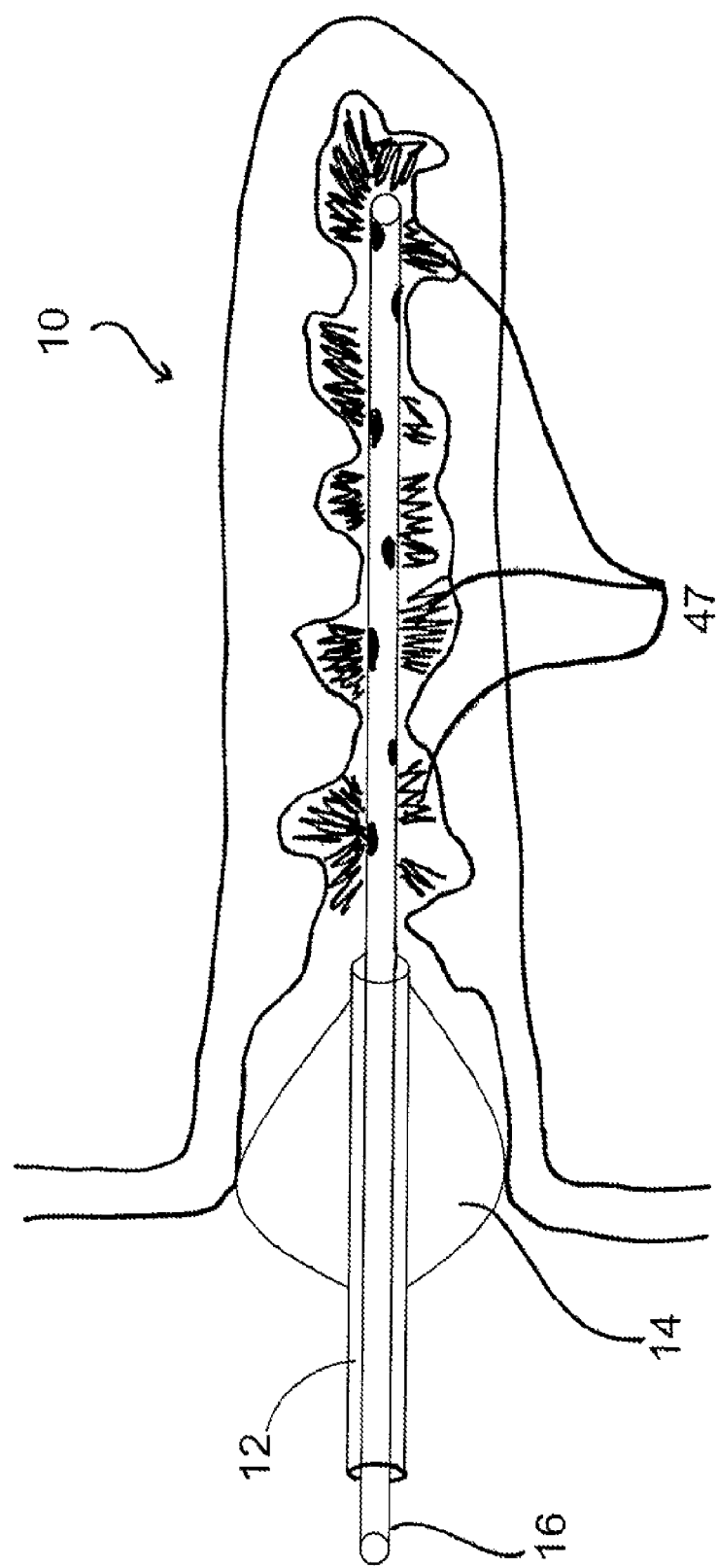
Figure 2D:
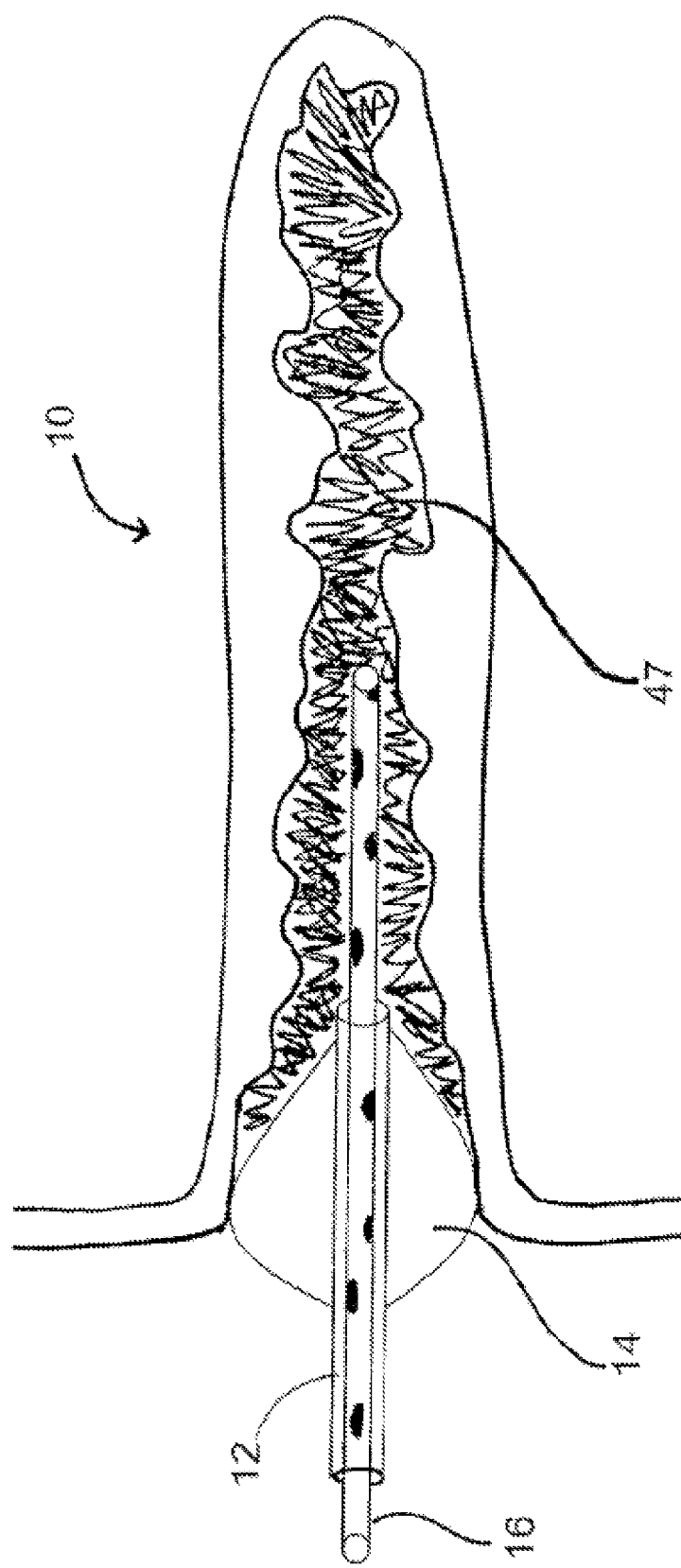
Figure 2E:
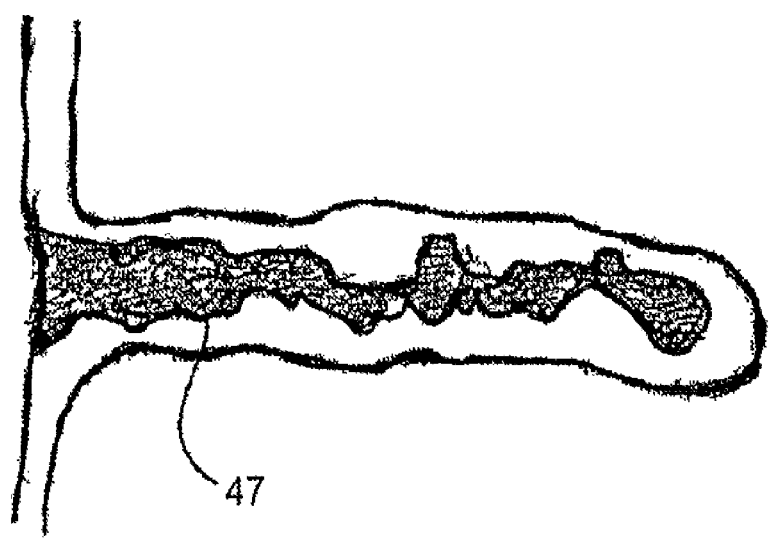

As shown in FIG. 2C, the application of the adhesive 47 within the collapsed LAA functions to seal the LAA. Further, as the catheter 16 delivers the adhesive 47 into the LAA cavity, the catheter 16 is slowly withdrawn through the interior 24 of the shaft 12 (FIG. 2D). After the adhesive 47 has completed sealing, the balloon 14 is deflated. Thereafter, the left atrium of the heart can be injected with dye in order to show angiographically the LAA occlusion. Once the success of the procedure has been confirmed, the shaft 12 and the balloon 14 are withdrawn from the body, across the interatrial septum and back through the femoral vein, thereby leaving the cavity of LAA sealed as shown in FIG. 2E.

Now referring to FIG. 3, an additional embodiment of an occlusion assembly 100 is shown. The occlusion assembly 100 comprises the shaft 12 and the balloon 14, and a catheter needle 118. The shaft 12 and the balloon 14 are configured identically to the shaft 12 and the balloon 14 of the occlusion assembly 10. Accordingly, configuration of the shaft 12 and the balloon 14 will not be described in detail with respect to the occlusion assembly 100, and like reference numerals between FIGS. 1A-2E and FIGS. 3A-3D will refer to like components.

The catheter needle 118 of the occlusion assembly 100 comprises a catheter 116 comprising a proximal end 130, a distal end 132, a hollow interior 134, and one or more needle wires 121. The catheter 116 may be composed of any material known in the medical arts suitable for application within the heart. The hollow interior 134 of the catheter 116 extends the length of the catheter 116, and in one embodiment, the interior 134 of the catheter 116 comprises at least two independent lumens.

The needle wires 121 are coupled with the distal end 132 of the catheter 116 and extend therefrom. The needle wires 121 are hollow so that a magnetic glue-like substance or other suitable substance (not shown) can pass therethrough. In one embodiment, each of the needle wires 121 comprise a lumen extending the length of the needle wire 121 and a distal needle aperture 123 in communication with the lumen. The needle wires 121 may be composed of any suitable material commonly used in the medical arts that serves the functions noted herein including, without limitation, a metallic compound. In one embodiment, the needle wires 121 are comprised of a very fine, hollow wire.

Figure 3A:
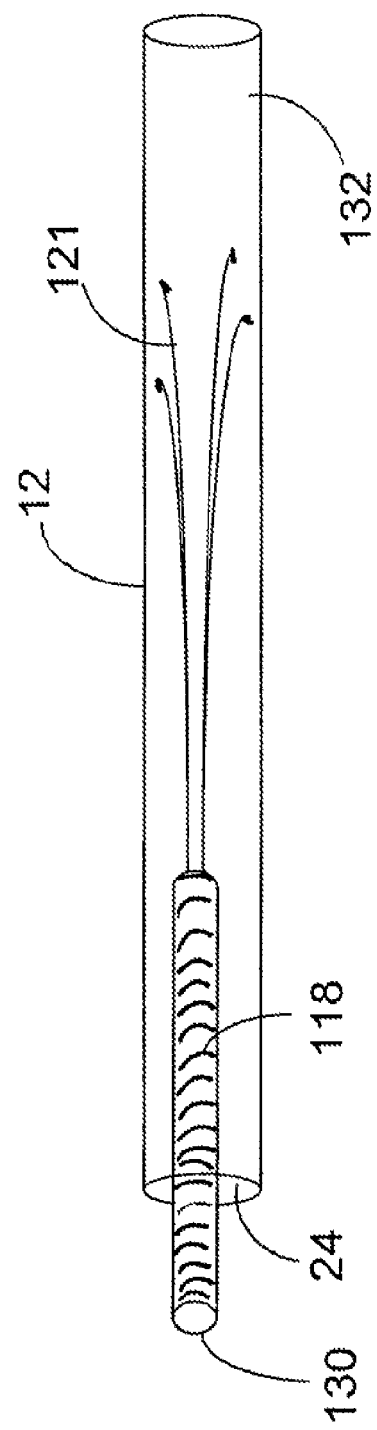
FIG. 3A shows a side view of at least one embodiment of an occlusion assembly.
Figure 3B:
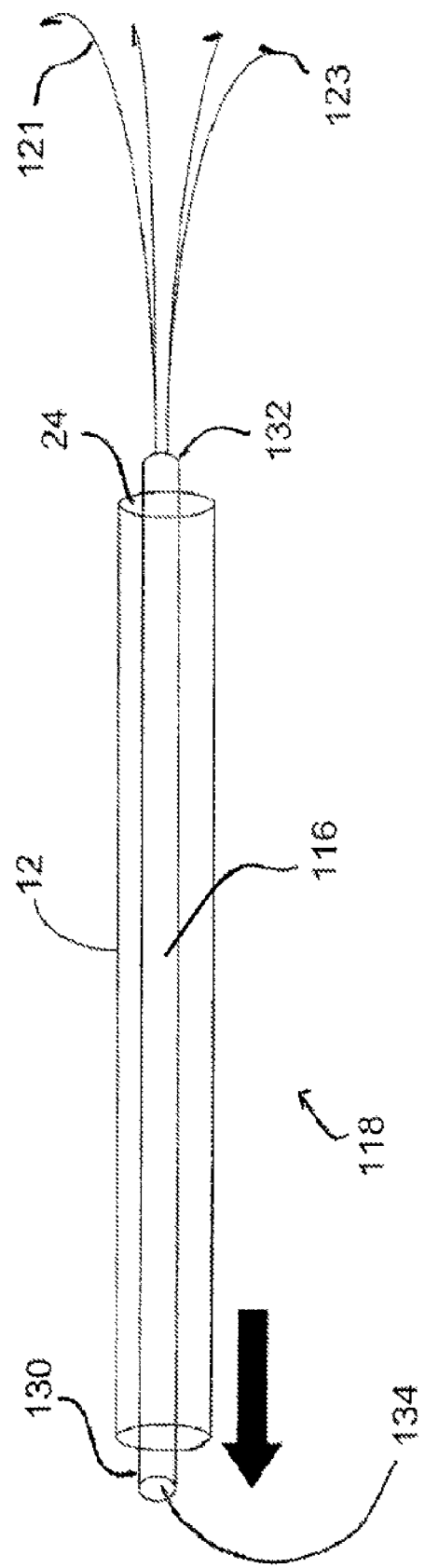

The catheter needle 118 can be slidably positioned within the interior 24 of the shaft 12. When the needle wires 121 of the catheter needle 118 are encased within the interior 24 of the shaft 12, the needle wires 121 are necessarily in a closed, joined form. In this manner, a clinician can effectively manipulate the catheter needle 118 containing the needle wires 121 in and around a patient's body without the needle wires 121 protruding and contacting surrounding tissue. However, once the catheter needle 118 is properly positioned (e.g., within the atrial appendage), a clinician may advance the catheter needle 118 through the distal end 22 of the shaft 12, thereby exposing the needle wires 121 and allowing them to expand as shown in FIG. 3B.

The lumen of each of the needle wires 121 is in communication with the hollow interior 134 of the catheter 116. In the embodiment where the catheter 116 comprises at least two independent lumens, the lumens of each of the needle wires 121 may be in communication with one of the lumens of the catheter 116, some of the lumens of the catheter 116, or all of the lumens of the catheter 116. In one embodiment, the lumen of each needle wire 121 is in communication with each of the lumens of the catheter 116. In this manner, a first lumen of the catheter 116 may provide a suctional force through the lumen of the needle wire 121, and a second lumen of the catheter 116 may provide delivery of an adhesive or medicament through the lumen of the needle wire 121. Alternatively, and in the same manner, a first lumen of the catheter 116 may provide a first adhesive to the needle wire 121 and a second lumen of the catheter 116 may provide a second adhesive to the needle wire 121.

As previously described, the needle wires 121 comprise a distal aperture 123. The distal aperture 123 is in communication with the lumen of the needle wire 118, and as such, in communication with the interior 134 of the catheter 116. In this manner a magnetic glue-like substance can be advanced through the interior of the catheter 116, into the lumen of the needle wire 118, and delivered to a targeted tissue through the needle aperture 123. Alternatively, a suctional force can be transmitted through the needle aperture 123. In one embodiment, the needle wires 121 are connected to an injection apparatus (not shown) for glue delivery via the hollow interiors of the needle wires 121, and a vacuum source (not shown) to supply the requisite suction necessary to aspirate the LAA cavity.

The needle wires 121 may further have an expanded memory. For example, the needle wires 121 may be initially closed and then expanded once exposed to a particular temperature or other stimuli. In other words, the needle wires 121 may comprise an original configuration, which may include, without limitation, a bend and/or a curve in the needle wires 121. When the needle wires 121 exhibiting their original configuration are positioned within the shaft 12, the original configuration may be altered (e.g., the needle wires 121 may be straightened while positioned within the interior of the shaft 12). When the needle wires 121 are thereafter protracted from the distal end 22 of the shaft 12, the original configuration of the needle wires 121 may then present itself.

The occlusion assembly 100 may be used in conjunction with an injection apparatus and a magnetic glue-like substance capable of injection by the injection apparatus. The injection apparatus may comprise any device capable of advancing a magnetic glue-like substance into the needle wires 121. The magnetic glue-like substance may exert a sufficient magnetic force so that when the magnetic glue-like substance is positioned on the exterior wall of an atrial appendage, the magnetic glue-like substance functions to effectively collapse the structure of the atrial appendage. The magnetic glue-like substance can be composed of any commonly used adhesive substance known in the medical arts.

In operation, the occlusion assembly 100, the shaft 12 and balloon 14 are delivered and deployed as previously described. Specifically, the balloon 14 is inflated and positioned to collect occluding the ostium of the LAA. Thereafter, the catheter needle 118 is delivered through the interior 24 of the shaft 12 (see FIG. 3A) and suction of the LAA cavity is initiated. In one embodiment, the suction can be provided through the needle apertures 123 of the needle wires 121. In an alternative embodiment, a vacuum source can be applied directly to the proximal end 20 of the shaft 12. The suctional force of the vacuum is maintained and/or increased until an amount of blood is removed from the LAA cavity and the LAA wall collapses. Even after the wall collapses, a degree of suction is maintained through the catheter 116 or the shaft 12 in order to ensure the balloon 14 maintains optimal position.

Figure 3D:
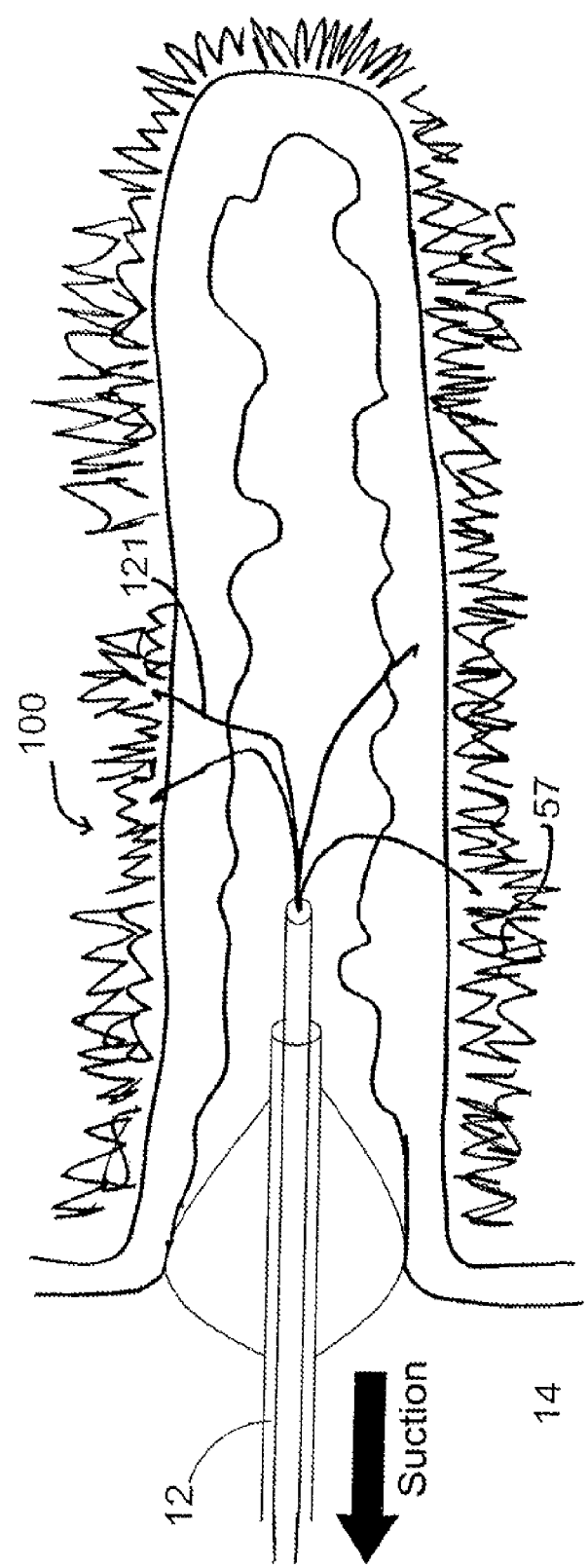
Figure 3E:
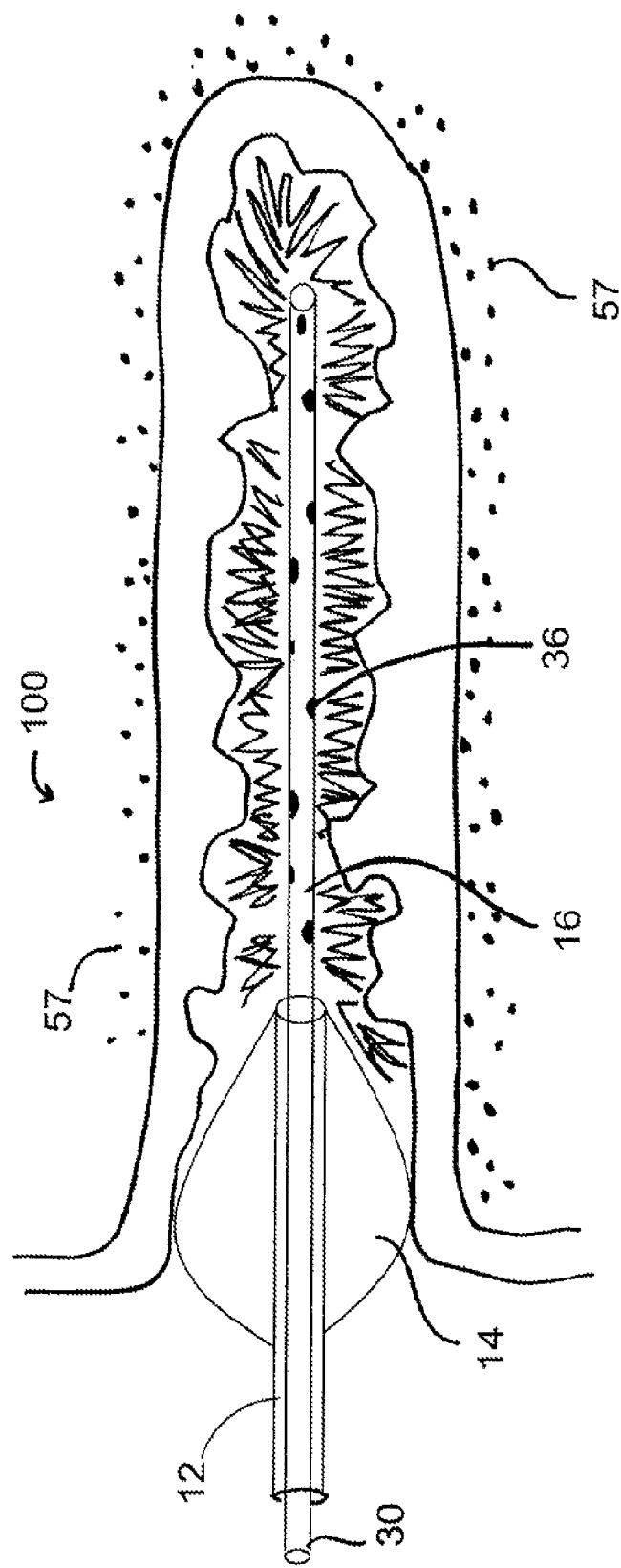
FIG. 3E shows a side view of at least one embodiment of an occlusion assembly as applied to treat a left atrial appendage.
Figure 3F:
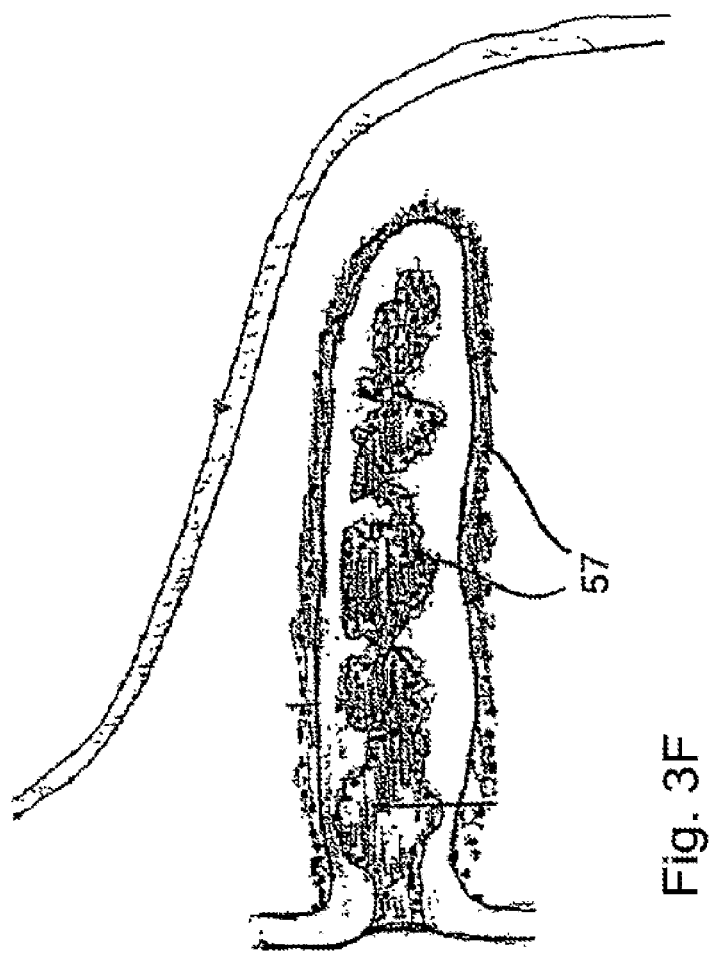
FIG. 3F shows a side view of a left atrial appendage that has been occluded using the occlusion assembly of FIGS. 3A-E.

Under fluoroscopic and transesophageal echocardiography control, the catheter needle 118 is advanced through the distal end 22 of the shaft 12 and the walls of the LAA are punctured with the needle wires 121 (see FIG. 3D). The needle wires 121 are capable of completely puncturing the LAA wall, such that the needle apertures 123 of the needle wires 121 are positioned within the pericardial sac. Due to the relatively thin nature of the needle wires 121, the puncture of the LAA wall has minimal effect on the pressure within the LAA cavity. However, in one embodiment, the suctional pressure may be slightly increased during this step to facilitate a constant pressure within the LAA cavity.

While the needle apertures 123 are positioned within the pericardial sac, an amount of magnetite microbeads 57 are delivered through the needle apertures 123 of the needle wires 121 onto the epicardial surface. In one embodiment, this delivery is achieved through the use of the injection apparatus previously described. The magnetite microbeads 57 may be delivered as an adhesive solution, a powder, or as carbon dioxide spray. As shown in FIG. 3D, after the first application is complete, the needle wires 121 are used to puncture the LAA and deliver the microbeads 57 to the epicardial surface in multiple locations. Once a sufficient amount of magnetite microbeads 57 have been applied to the external surface of the atrial appendage, the needle catheter 118 may be withdrawn through the shaft 12 and removed from the body. Alternatively, prior to being withdrawn, the needle catheter 118 may deposit an amount of magnetite microbeads 57 within the interior of the LAA cavity such that the magnetite microbeads 57 are distributed between the LAA wall trabecules (pectinate muscles). The catheter 16 (as shown in FIGS. 1A-1E) is thereafter introduced into the LAA cavity and an adhesive biological glue is injected therein to achieve an adequate seal of the LAA ostium (see FIG. 3E).

The inflation of the balloon 14 is maintained during the requisite sealing time and the catheter 16 is withdrawn from the body through the shaft 12. The magnetic attraction between the magnetic beads 57 on the epicardial surface of the LAA and the magnetite beads 57 disposed within the interior of the LAA functions to create a constricted and tightened LAA, thereby promoting the occlusion of the LAA (see FIG. 3F).

Figure 4A:
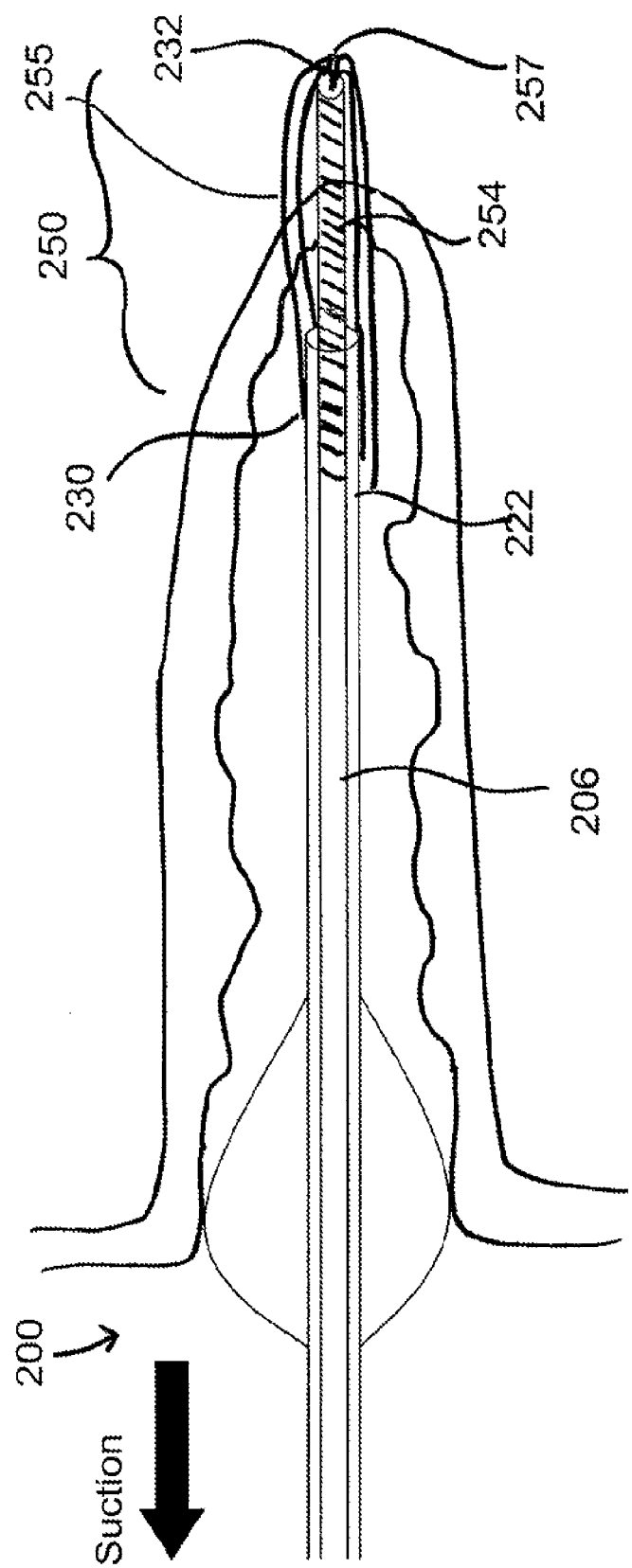
FIGS. 4A-4B show two side views of at least one embodiment of an occlusion assembly as applied to treat a left atrial appendage.
Figure 4B:
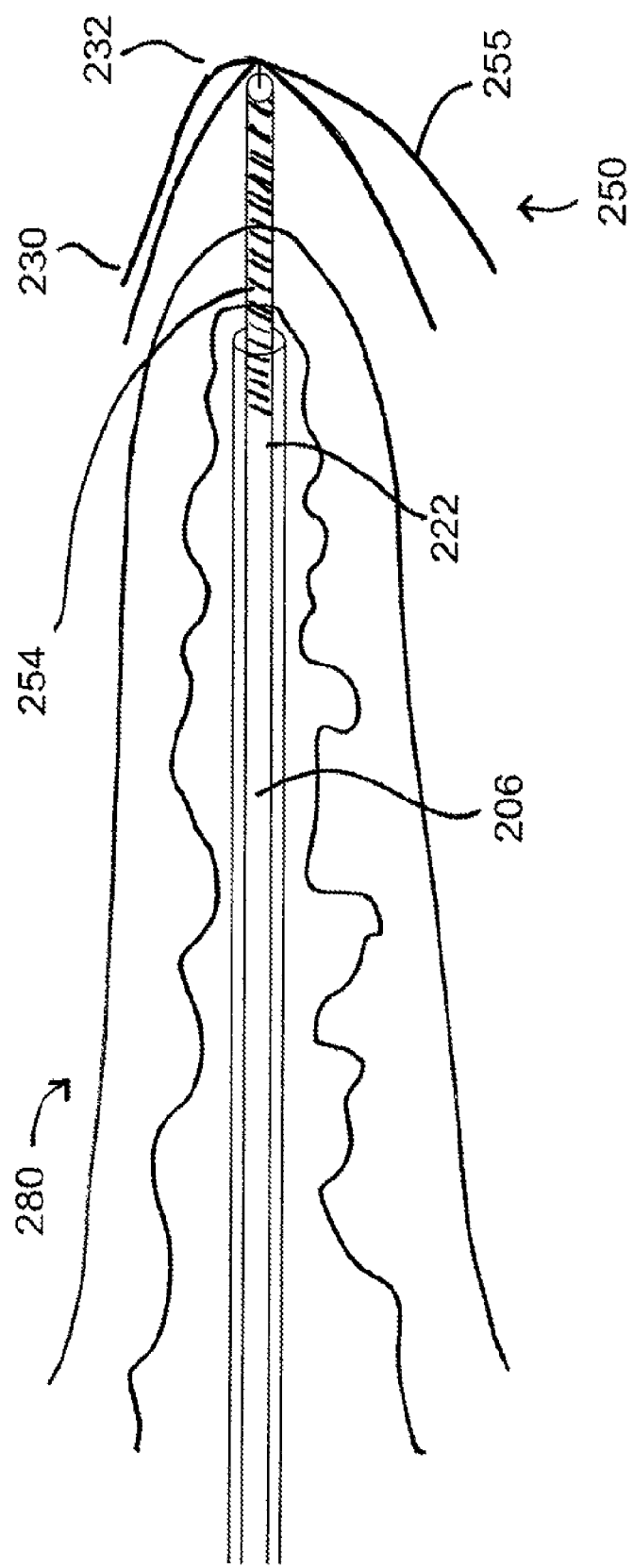

Now referring to FIGS. 4A and 4B, another embodiment of an occlusion assembly 200 is shown. The occlusion assembly 200 comprises the shaft 12 and the balloon 14, and a catheter 216. The shaft 12 and the balloon 14 are configured identically to the shaft 12 and the balloon 14 of the occlusion assembly 10. Accordingly, configuration of the shaft 12 and the balloon 14 will not be described in detail with respect to the occlusion assembly 100, and like reference numerals between FIGS. 1A-2E and FIGS. 4A-4B will refer to like components.

In one embodiment, a catheter 216 is used in conjunction with the shaft 12 and the balloon 14 to collapse an atrial appendage. The catheter 216 comprises a proximal end 220, a distal end 222, and a clip assembly 250 extending from the distal end 222 of the catheter 216. The clip assembly 250 comprises a magnetic bar 254 and a plurality of ferromagnetic clips 255 positioned in an umbrella-like configuration. The magnetic bar 254 is removably coupled with the distal end 222 of the catheter 216 such that once the clip assembly 250 is anchored to a tissue, the catheter 216 can be removed therefrom and withdrawn from the body. Further, in at least one embodiment, the magnetic bar 254 initially comprises a sheath disposed thereon to prevent any magnetic attraction between the ferromagnetic clips 255 and the magnetic bar 254 prior to deployment of the device.

Each of the ferromagnetic clips 255 comprising the clip assembly 250 comprises a first end 230 and a second end 232. In addition, each of the ferromagnetic clips 255 exhibits a magnetic polarity. The second ends 232 of the ferromagnetic clips 255 are hingedly coupled with the magnetic bar 254, such that a hinged apex 257 is formed. From this hinged apex 257, the clip assembly 250 is capable of moving between a compressed position (closed umbrella) and an expanded position (open umbrella).

The ferromagnetic clips 255 are specifically arranged around the magnetic bar 257 such that ferromagnetic clips 255 a magnetic force is generated between the components of the clip assembly 250. However, for as long as the sheath is disposed on the magnetic bar 254, the various components of the clip assembly 250 may be easily maneuvered.

When the clip assembly 250 is positioned in a compressed position, each of the ferromagnetic clips 255 lay substantially parallel with the catheter 116 (see FIG. 4A). In addition, the apex 257 of the assembly 150 comprises a needle-like surface that is capable of puncturing a targeted tissue. When the ferromagnetic clips 255 are positioned in the expanded position, the first ends 230 of the clips 255 extend radially from the magnetic bar 257 such that the ferromagnetic clips 255 are positioned in the expanded position (see FIG. 4B).

The umbrella-like configuration of the clip assembly 250 enables the clip assembly 250 to puncture a targeted tissue and subsequently anchor thereto. For example, when the ferromagnetic clips 255 are positioned in the compressed position, the apex 257 of the clip assembly 250 can be used to puncture the tissue of the LAA. Thereafter, the ferromagnetic clips 255 in the compressed position are advanced through the puncture hole and into the pericardial space. Once the first ends 230 of the ferromagnetic clips 255 clear the puncture hole in the tissue, the catheter 216 is withdrawn through a pull back technique. As the first ends 230 of the ferromagnetic clips 255 are not as tightly configured as are the second ends 232 which form a needle-like tip, the first ends 230 cannot retract through the puncture hole in the tissue. Accordingly, the first ends 230 of the ferromagnetic clips 255 to expand radially away from the catheter 216 and into the expanded position.

Figure 5A:
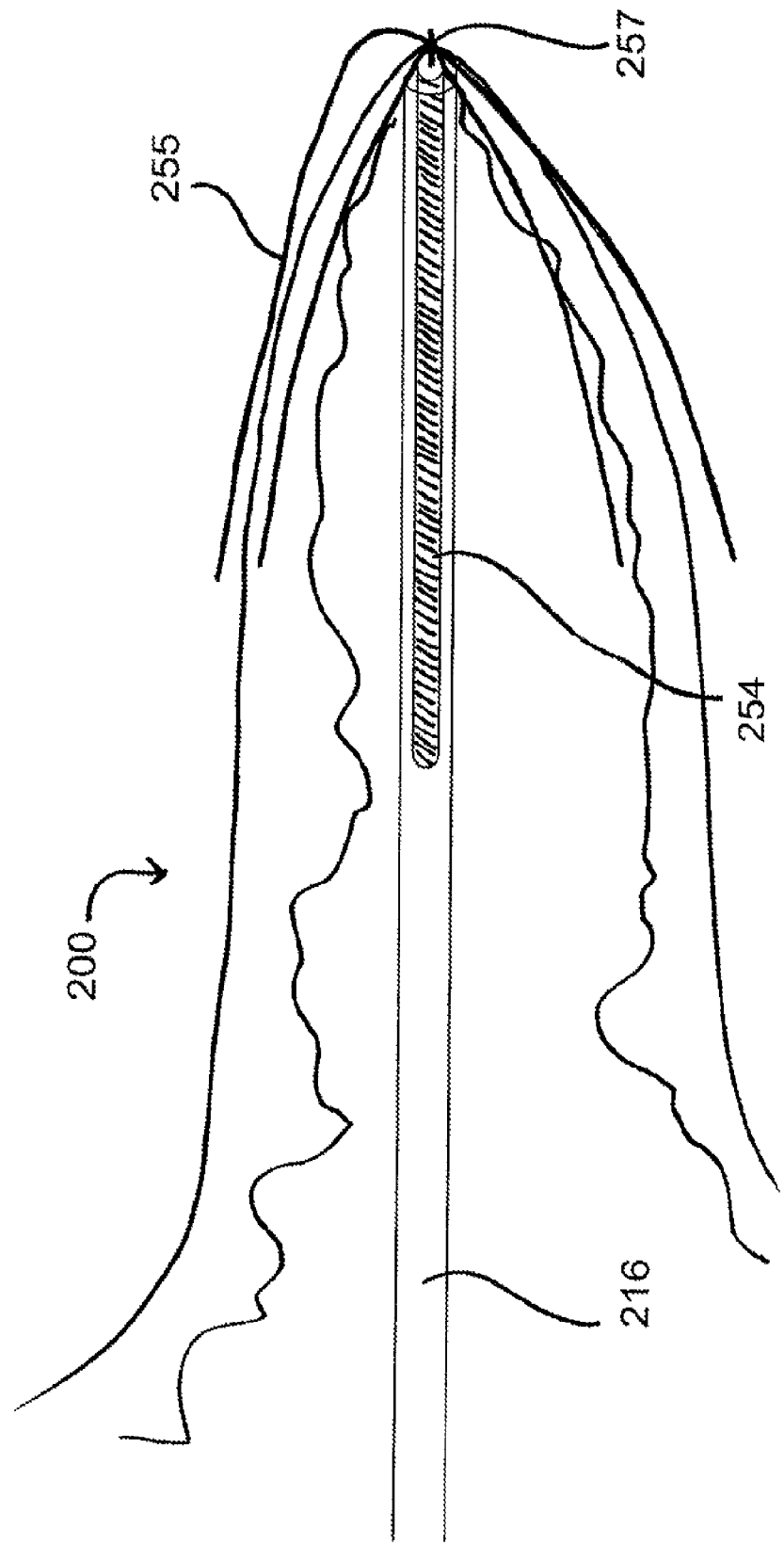
FIGS. 5A, 5B, and 5C show side views of the occlusion assembly of FIGS. 4A-4B in operation.
Figure 5B:
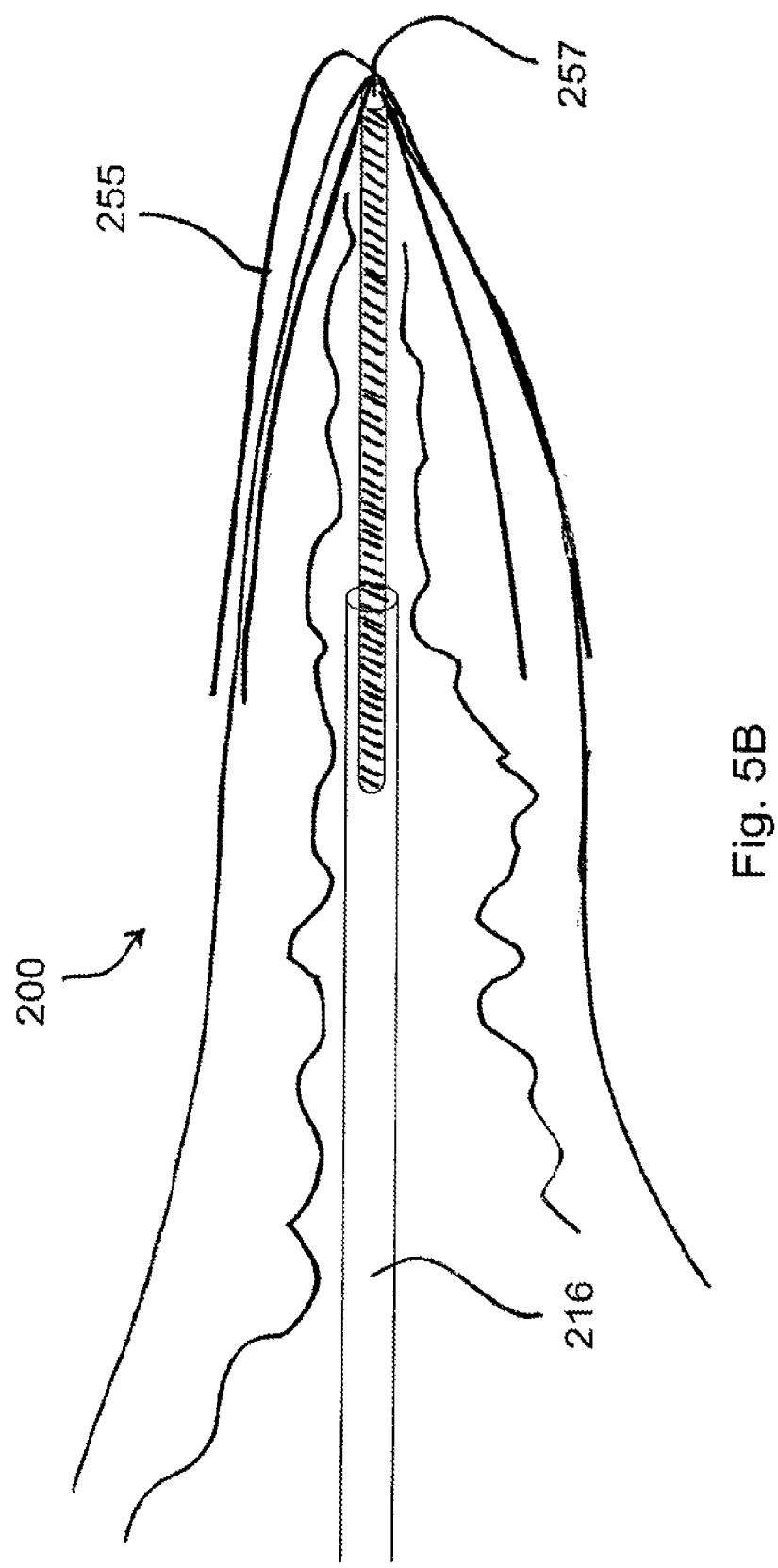
Figure 5C:
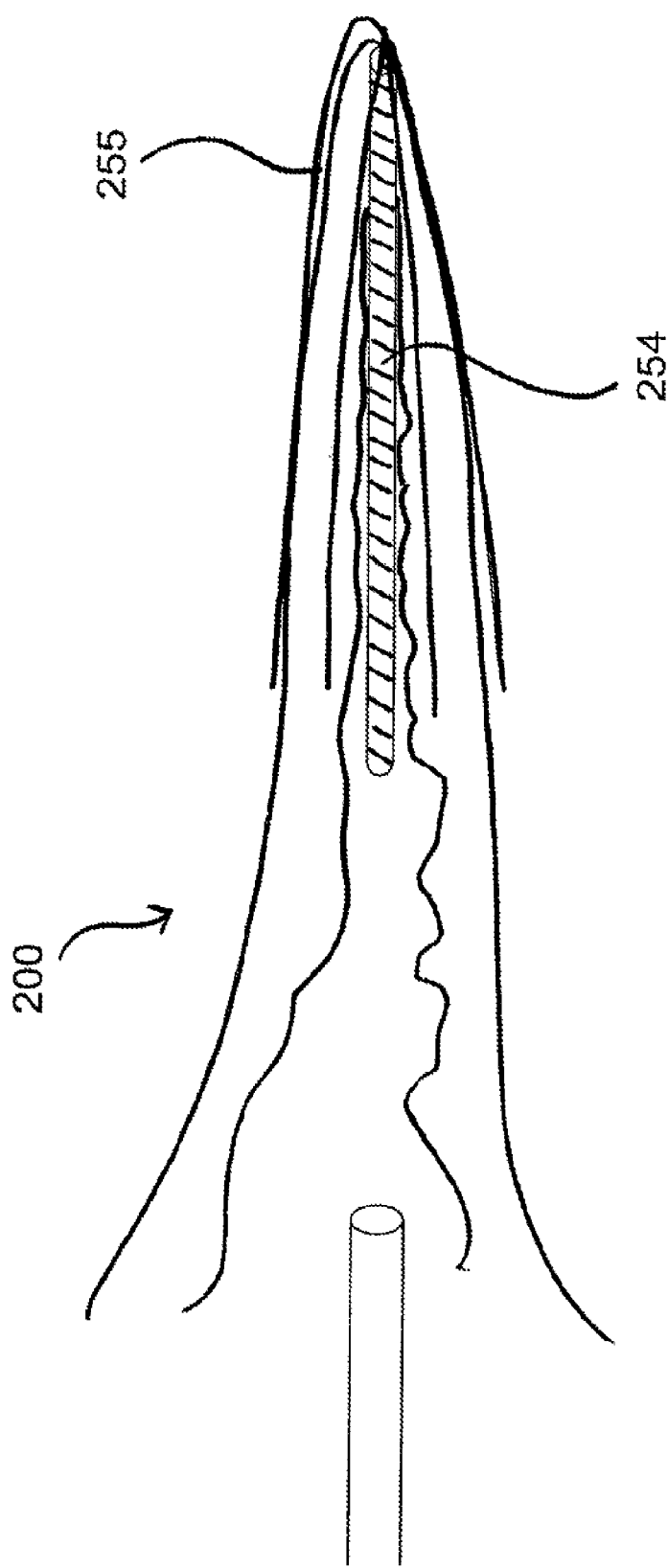

The magnetic bar 254 remains positioned within the interior of the LAA. At this point, the sheath disposed on the magnetic bar 254 to prevent magnetic interaction between the magnetic bar 257 and the ferromagnetic clips 255 is removed. Once the sheath is removed, the magnetic attraction between the components of the clip assembly 250 causes the ferromagnetic clips 255 to move into the compressed position, thereby applying pressure to the exterior of the LAA as shown in FIGS. 5A-5C. In this manner, a sandwich effect is created around the exterior of the LAA and the LAA cavity is caused to collapse. Once the desired collapse has been achieved, the catheter 216 may be uncoupled from the magnetic bar 257 (through unscrewing or some other means) and withdrawn from the body.

Now referring to FIGS. 6A-9B, at least one embodiment of an occlusion assembly 300 is shown. The occlusion assembly 300 comprises the shaft 12, the balloon 14, a catheter 316, a needle wire 318, and a memory wire 320. The shaft 12 and the balloon 14 are configured identically to the shaft 12 and the balloon 14 of the occlusion assembly 10. Accordingly, configuration of the shaft 12 and the balloon 14 will not be described in detail with respect to the occlusion assembly 300, and like reference numerals between FIGS. 1A-2E and FIGS. 6A-9B will refer to like components.

Figure 6A:
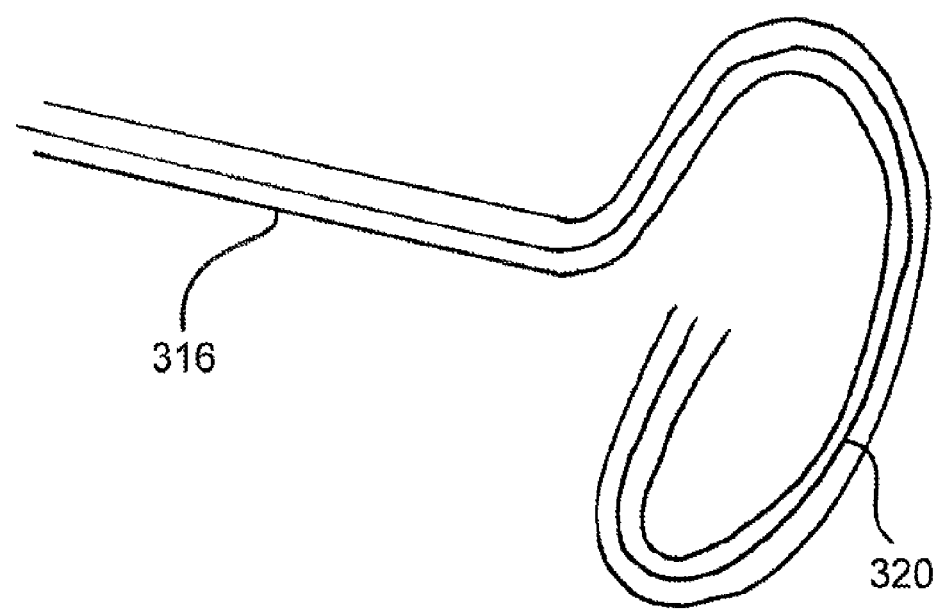
FIGS. 6A-6C show various embodiments of a pigtail catheter that may be used to treat a left atrial appendage.
Figure 6B:
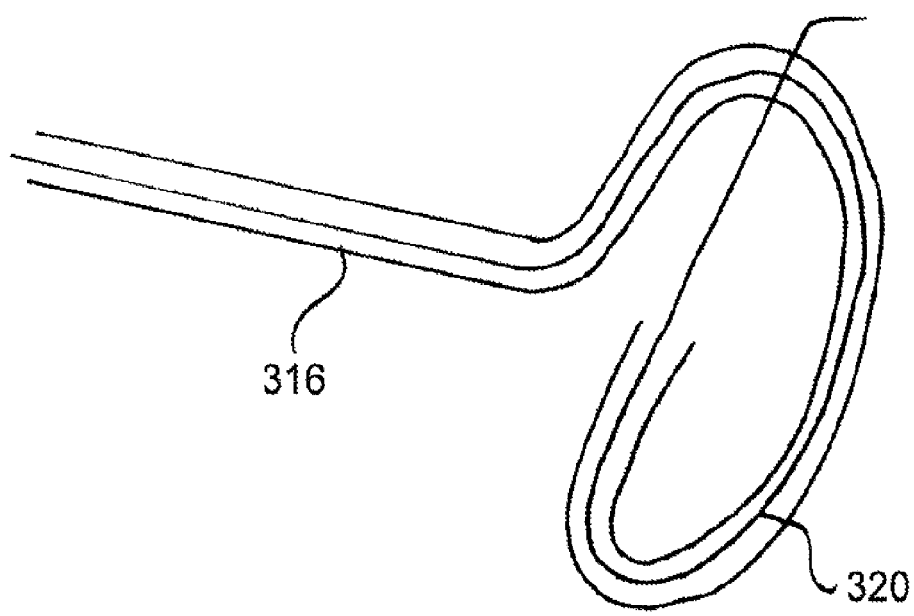
Figure 6C:
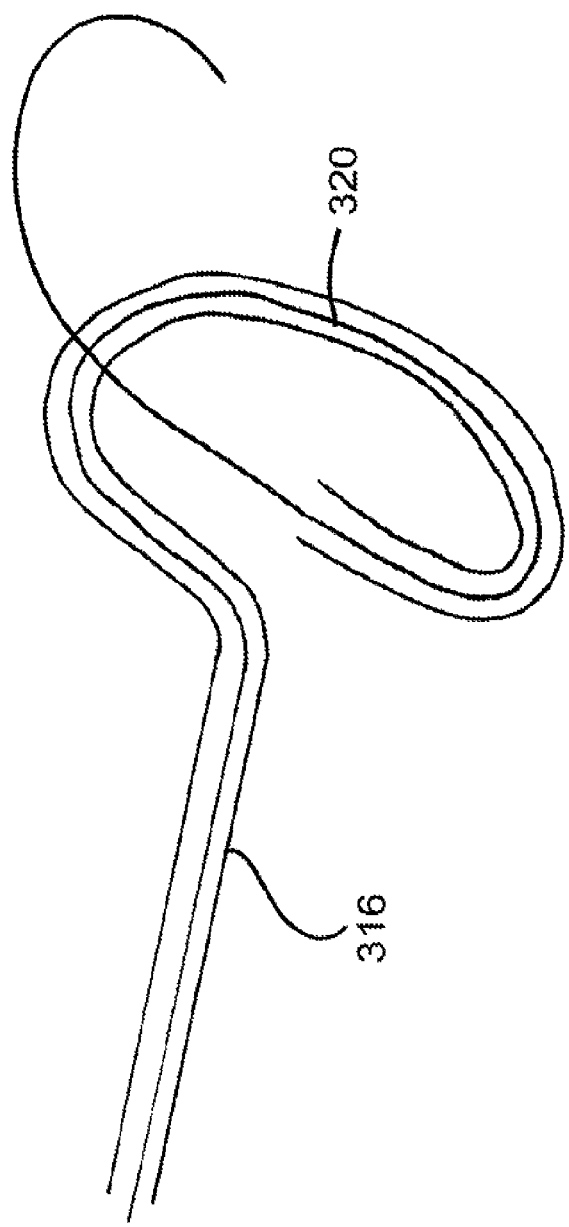
Figure 9B:
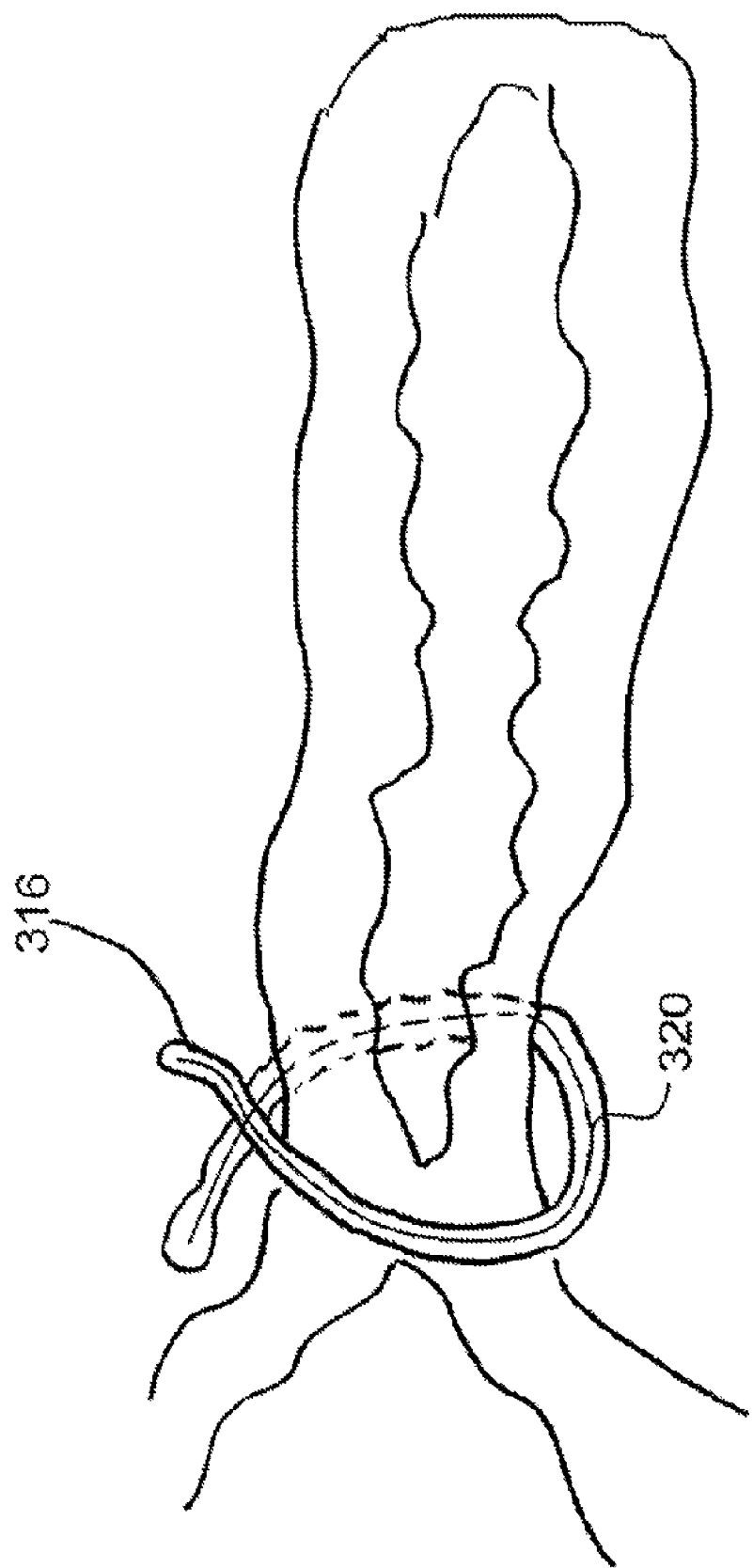

The occlusion assembly 300 comprises a catheter 316, a needle wire 318, and a memory wire 320. The catheter 316 comprises a preformed pigtail catheter having a plurality of lumens. FIGS. 6A-6C illustrate various configurations of the catheter 316, although the catheter 316 may comprise any other configuration capable of advancing the memory wire 320 through the base of the LAA. In one embodiment, the catheter 316 comprises three lumens: a first lumen coupled with a vacuum device, a second lumen for receiving a guide wire, and a third lumen for receiving the memory wire 320 and the needle wire 318. The memory wire 320 may be made of a shape memory alloy, such as nitinol. Thus, the wire 320 is relatively straight when deployed through the catheter 316. However, after introduction into the body and placement around the atrial appendage, by manipulating the wire to wrap around the appendage, the wire forms the shape of a loop. In one embodiment, the memory wire 320 is relatively short and is employed with a separate wire guide to facilitate accurate placement.

The catheter 316 is delivered into the LAA and suction is applied thereto as previously described herein. The needle wire 318 is advanced through the shaft 12, and is used to puncture the base of the LAA, as shown in FIG. 7. After the LAA wall is punctured, the atraumatic guide wire 18 is introduced into the puncture hole and advanced through the LAA wall and into the pericardial space. Once the puncture hole is maintained by the guide wire 18, the needle wire 318 is withdrawn back into the LAA and thereafter removed from the body.

The catheter 316 is then advanced, following the guide wire 18, through the puncture in the LAA wall. Further, the pigtail configuration of the catheter 316 is utilized to wrap around the base of the LAA, as shown in FIG. 8. At this point, the guide wire 18 is withdrawn and removed, and the wire guide is advanced in its place. The wire guide functions to push and deliver the short memory wire 320 to the base of the LAA. Accordingly, the wire guide effects the placement of the memory wire 320 through pushing and pulling the memory wire 320 around the base of the LAA as shown in FIG. 9. In this manner, the two ends of the memory wire 320 are crossed around the base of the LAA. Concurrent with the manipulation of the memory wire 320, the catheter 316 is slowly withdrawn from the LAA cavity through the shaft 12. Due to the shape memory alloy properties of the memory wire 320 and its placement around the base of the LAA, the memory wire 320 effectively occludes the LAA without the use of adhesives or sutures.

While various embodiments of devices, systems, and methods for occluding the LAA have been described in considerable detail herein, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or to limiting. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that this description and the appended claims will encompass, all modifications and changes apparent to those of ordinary skill in the art based on this disclosure.

The invention claimed is:

1. A method for occluding an atrial appendage comprising the steps of:
    providing a device for occluding an atrial appendage comprising:
        a shaft comprising a first hollow interior, an exterior surface, a first open end, a second open end, and an inflatable balloon coupled to the exterior surface,
        a catheter slidably positioned within the first hollow interior of the shaft, the catheter comprising a proximal end, a distal end, an exterior surface, a second hollow interior, and at least one opening communicating from the second hollow interior to the exterior surface adjacent to the distal end,
        a vacuum source operatively coupled with the second hollow interior of the catheter and capable of providing suction through the at least one opening, and
        an adhesive delivery device operatively coupled with the second hollow interior of the catheter and capable of delivering an adhesive through the at least one opening,
        wherein the inflatable balloon is configured to seal an ostium of the atrial appendage when the device is positioned within the atrial appendage and the balloon is inflated, and operation of the vacuum source creates a vacuum within the sealed atrial appendage, thereby causing the atrial appendage to collapse, and
        wherein the vacuum source is capable of providing suction through the second open end;
    delivering the shaft and catheter to the atrial appendage through a percutaneous intravenous route;
    inflating the balloon at the ostium of the atrial appendage such that the ostium is sealed;
    puncturing the walls of the atrial appendage at a first location by advancing the catheter through the second open end of the shaft; and
    collapsing the walls of the atrial appendage through operation of the vacuum source while the balloon is inflated to seal the ostium of the atrial appendage.

2. The method of claim 1, further comprising the step of:
    injecting an adhesive into the collapsed atrial appendage, thereby sealing the collapsed atrial appendage.

3. The method of claim 2, wherein the step of injecting an adhesive into the collapsed atrial appendage further comprises:
    advancing the distal end of the catheter into the atrial appendage; and
    operating the adhesive delivery device such that an amount of adhesive advances through the second hollow interior of the catheter and through the at least one opening.

4. The method of claim 2, wherein the step of operating the adhesive delivery source is performed to fill the collapsed atrial appendage with the adhesive.

5. The method of claim 2, further comprising the steps of:
    deflating the balloon; and
    withdrawing the shaft and catheter.

6. The method of claim 1, wherein delivering the shaft and catheter to the atrial appendage further comprises the step of performing transseptal procedure.

7. The method of claim 1, wherein the step of collapsing the walls of the atrial appendage through operation of the vacuum source further comprises:
    advancing the distal end of the catheter into the atrial appendage; and
    applying suction to the interior of the atrial appendage through the at least one opening of the catheter.

8. The method of claim 1, further comprising the step of:
    puncturing the walls of the atrial appendage at a second location by advancing the catheter through the second open end of the shaft.

9. The method of claim 1, further comprising the steps of:
    delivering a first adhesive to the exterior walls of the atrial appendage; and
    delivering a second adhesive to the interior walls of the atrial appendage.

10. The method of claim 9, wherein the first adhesive comprises a magnetic adhesive having a first polarity, and the second adhesive comprises a magnetic adhesive comprising a second polarity.

11. The method of claim 9, wherein the step of delivering a second adhesive to the exterior walls of the atrial appendage further comprises the steps of:
    providing a device comprising:
        a second catheter slidably positioned within the first hollow interior of the shaft, the second catheter comprising a distal end, an interior, and at least one opening disposed through the distal end,
        wherein the adhesive delivery device is operatively coupled with the interior of the second catheter and capable of delivering the second adhesive through the at least one opening in the second catheter;
    withdrawing the first catheter from the first hollow interior of the shaft;
    injecting the second adhesive into the collapsed atrial appendage; and
    sealing the collapsed atrial appendage.

12. A method for occluding an atrial appendage, comprising the steps of:
    percutaneously and intravascularly introducing a portion of a device for occluding an atrial appendage through a blood vessel, into a heart, and into the atrial appendage, the device comprising:
        a shaft defining a first hollow interior therethrough, an exterior surface, a first open end, a second open end, and having an inflatable balloon coupled thereto, the inflatable balloon configured to seal an ostium of the atrial appendage upon inflation;
        a catheter slidably positioned within the first hollow interior of the shaft, the catheter comprising a proximal end, a distal end, an exterior surface, and defining a second hollow interior therethrough and at least one opening at or near a distal end of the catheter in communication with the second hollow interior;
        an adhesive delivery device coupled with the second hollow interior of the catheter and configured to deliver an adhesive through the at least one opening; and a vacuum source operatively coupled with the second hollow interior of the catheter and capable of providing suction through the at least one opening;

wherein the inflatable balloon is configured to seal an ostium of the atrial appendage when the device is positioned within the atrial appendage and the balloon is inflated, and operation of the vacuum source creates a vacuum within the sealed atrial appendage, thereby causing the atrial appendage to collapse; and wherein the vacuum source is capable of providing suction through the second open end;

positioning the balloon at the ostium of the atrial appendage; and inflating the balloon to seal the ostium;

puncturing the walls of the atrial appendage at a first location by advancing the catheter through the second open end of the shaft; and collapsing the walls of the atrial appendage through operation of the vacuum source while the balloon is inflated to seal the ostium of the atrial appendage.

13. The method of claim 12, further comprising the step of:

injecting an adhesive into the collapsed atrial appendage to seal the collapsed atrial appendage.

14. The method of claim 13, further comprising the step of:

removing the shaft and catheter from the sealed atrial appendage.

* * * * *